United States Patent
Cho et al.

(10) Patent No.: US 9,345,568 B2
(45) Date of Patent: May 24, 2016

(54) RETINAL PROSTHESIS SYSTEM USING NANOWIRE LIGHT DETECTOR, AND MANUFACTURING METHOD THEREOF

(75) Inventors: Dong Il Cho, Seoul (KR); Suk Won Jung, Gyeonggi-do (KR); Sang Min Lee, Seoul (KR); Sun Kil Park, Gyeonggi-do (KR); Jae Hyun Ahn, Seoul (KR); Seok Jun Hong, Seoul (KR); Hyoung Jung Yoo, Daegu (KR)

(73) Assignee: SNU R&DB FOUNDATION, Seoul (KR)

( * ) Notice: Subject to any disclaimer, the term of this patent is extended or adjusted under 35 U.S.C. 154(b) by 158 days.

(21) Appl. No.: 13/983,518

(22) PCT Filed: May 4, 2012

(86) PCT No.: PCT/KR2012/003527
§ 371 (c)(1),
(2), (4) Date: Aug. 2, 2013

(87) PCT Pub. No.: WO2012/157877
PCT Pub. Date: Nov. 22, 2012

(65) Prior Publication Data
US 2013/0310933 A1 Nov. 21, 2013

(30) Foreign Application Priority Data
May 16, 2011 (KR) .................. 10-2011-0045783

(51) Int. Cl.
*A61F 2/14* (2006.01)
*A61N 1/05* (2006.01)
*A61N 1/36* (2006.01)

(52) U.S. Cl.
CPC ............... *A61F 2/14* (2013.01); *A61N 1/0543* (2013.01); *A61N 1/36046* (2013.01)

(58) Field of Classification Search
USPC ........................................ 623/6.63
See application file for complete search history.

(56) References Cited

U.S. PATENT DOCUMENTS

| 7,682,943 B2 * | 3/2010 | Samuelson ............ B82Y 10/00 438/478 |
| 2003/0032946 A1 | 2/2003 | Fishman et al. |

(Continued)

FOREIGN PATENT DOCUMENTS

KR 100444834 8/2004

OTHER PUBLICATIONS

Seung Woo Lee et al., "Development of Microelectrode Arrays for Artificial Retinal Implants Using Liquid Crystal Polyers", Investigate Opthalmology & Visual Science, 2009 vol. 50, No. 12, pp. 5859-5866.

(Continued)

*Primary Examiner* — David H Willse
*Assistant Examiner* — Javier Blanco
(74) *Attorney, Agent, or Firm* — McDermott Will & Emery LLP

(57) ABSTRACT

A retinal prosthesis system can comprise: a flexible substrate; a nanowire light detector which is placed on the substrate, and comprises one or more nanowires of which the resistance changes according to the applied light; one or more micro-electrodes which are placed on the substrate, are electrically connected to the nanowire light detector, and come in contact with retinal cells; and an electric power supply source for applying electric power to the nanowire light detector and the micro-electrodes. The retinal prosthesis system can be implemented into a very thin and flexible substrate type high resolution retinal system by manufacturing a nanowire light detector on a substrate in which micro-electrodes are implemented.

5 Claims, 26 Drawing Sheets

(56) References Cited

U.S. PATENT DOCUMENTS

| | | | |
|---|---|---|---|
| 2003/0097166 A1 | 5/2003 | Krulevitch et al. | |
| 2008/0288067 A1* | 11/2008 | Flood | A61N 1/0543 623/6.63 |
| 2011/0253982 A1* | 10/2011 | Wang | B82Y 10/00 257/24 |
| 2014/0128972 A1* | 5/2014 | Khraiche | A61L 27/18 623/6.63 |

OTHER PUBLICATIONS

Shu-Ping Lin et al., "Characterization of Surface Modification on Microelectrode Arrays for in Vitro Cell Culture", Biomed Microdevices, 2008, vol. 10, pp. 99-111.

J.A. Zhou et al., "A Suprachoroidal Electrical Retinal Stimulator Design for Long-Term Animal Experiments and in Vivo Assessment of Its Feasibility and Biocompatibility in Rabbits", Journal of Biomedicine and Biotechnology, 2008, vol. 2008, Article ID 547428, pp. 1-10.

\* cited by examiner

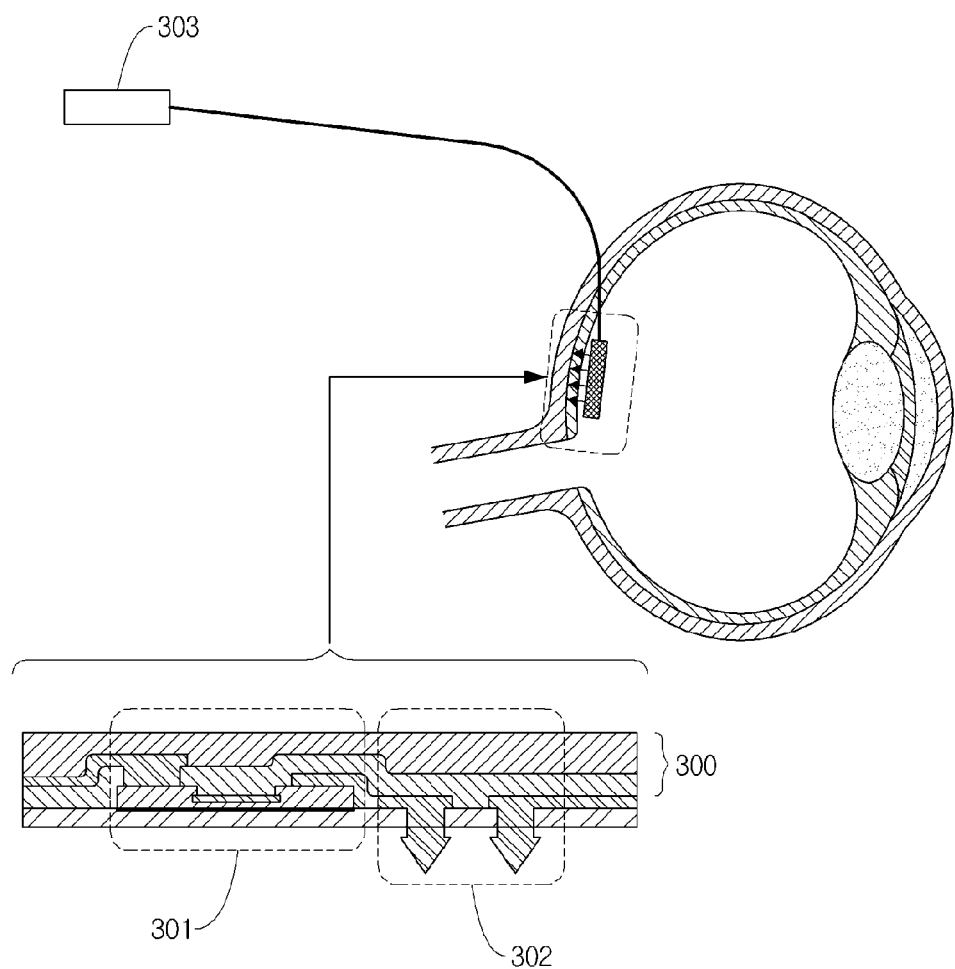

RETINAL PROSTHESIS SYSTEM USING NANOWIRE LIGHT DETECTOR, AND MANUFACTURING METHOD THEREOF

RELATED APPLICATIONS

This application is the U.S. National Phase under 35 U.S.C. §371 of International Application No. PCT/KR2012/003527, filed on May 4, 2012, which in turn claims the benefit of Korean Patent Application No. 10-2011-0045783, filed on May 16, 2011, the disclosures of which Applications are incorporated by reference herein.

TECHNICAL FIELD

Embodiments relate to a retinal prosthesis system and a method for manufacturing the same, and more particularly, to a retinal prosthesis system including a nanowire photodetector and at least one micro electrode to obtain image information and generate a retina stimulation signal simultaneously and a method for manufacturing the same.

BACKGROUND ART

The light reaching the eye of a human is converted into a bioelectric signal at a photoreceptor and transmitted to the visual cortex. In the case the photoreceptor is damaged, even though other nerve cells are alive, the light is not recognized. Such diseases are representatively retinis pigmentosa (RP) and age-related macular degeneration (AMD).

A retinal prosthesis system (or a visual prosthesis system) artificially transplants a micro electrode array in a retina cell in order to recover a vision of a disabled person who is visually impaired due to a retina damage, and applies an electric stimulation signal to the transplanted micro electrode array to cause an artificial electric stimulation at the retina cell, so that the electric stimulation signal is transmitted to the cerebrum and allows a person who has lost his sight due to a retina damage to recognize a sight.

The retinal prosthesis system generally includes an image information acquisition device, a signal processing and generating device, and a micro electrode array. The image information acquisition device converts image information into electric signals like an image sensor of a camera, and the signal processing and generating device converts the image signal obtained from the image information acquisition device into an electric stimulation signal for stimulating the retina cell. In addition, the micro electrode array is transplanted in a living body and contacts the retina cell, so that the electric stimulation signal generated by the signal generating device is transmitted to the retina cell to stimulate the retina cell. The micro electrode array may have a two-dimension (2D) structure having a simple planar shape or a sharp three-dimensional (3D) structure which may be embedded deep in the retina organization.

FIG. 1 shows an example of a general retinal prosthesis system. The retinal prosthesis system of FIG. 1 does not include an image sensor.

Referring to FIG. 1, the retinal prosthesis system acquires image information by using an image information acquisition device 101 which is worn by a human body or carried by a human. The image information acquired by the image information acquisition device 101 is transmitted to a signal processor 102, and the signal processor 102 converts the image information into an electric stimulation signal for stimulating the retina cell. The wireless implant 103 receives a signal from the signal processor 102 and transmits the received signal to a micro electrode array contacting the retina cell to stimulate the retina cell.

In the retinal prosthesis system, a device such as a camera is generally worn at a spot on the outside of a human body as the image information acquisition device 101. However, it is cumbersome to wear or carry such a device, and this gives many limitations in free activities of the human. In addition, in order to transmit the image information of an external camera to the micro electrode array transplanted on the eyeball, signals should be connected to the micro electrode array. However, as the micro electrode array has a higher resolution, the number of electrodes connected to the micro electrode array increases exponentially. Therefore, the wiring process is very complicated, and the electrodes should be arranged too densely. For this reason, there is a limit in enhancing the image resolution.

Meanwhile, separate from the image resolution problem, when acquiring image information, a normal person may naturally obtain desired image information by moving the eyeball, for example rotating the eyeball. However, in the general retinal prosthesis system shown in FIG. 1, image information should be acquired not by moving the eyeball but by moving the head or a part of the human body. Therefore, it is impossible to rapidly acquire image information, and the eyeball muscles are degraded since the human does not depend on the movement of the eyeball. This phenomenon is frequently found for persons who are visually impaired, and is called ophthalmodonesis.

FIG. 2 shows another example of a general retinal prosthesis system. The retinal prosthesis system of FIG. 2 includes an image sensor.

Referring to FIG. 2, the retinal prosthesis system may include an image sensor 201, a power source 202 for supplying power and signals, an internal cable 203, an external cable 204 and a plug 205 for electrically connecting the image sensor 201 and the power source 202, or the like. The retinal prosthesis system may acquire image information and stimulate the retina without using an external camera since the image sensor 201 for acquiring images is included therein.

In the retinal prosthesis system, since the image sensor 201 for acquiring image information is transplanted to the eyeball, image information may be acquired by moving the eyeball, without turning the head. Therefore, normal eyeball movement is ensured to eliminate a symptom such as ophthalmodonesis, and natural eyeball movement may be maintained. However, since the retina stimulating system is fabricated depending on a complementary metal-oxide semiconductor (CMOS) process, a 2D micro electrode array with a planar shape may be made, but a micro electrode array with a 3D shape is not easily made. In addition, the retina stimulating system is implemented on a rigid substrate such as a silicon substrate. Therefore, the retina stimulating system is not flexible and thus is not easily adhered and fixed to the eyeball.

DISCLOSURE

Technical Problem

In one aspect of the present disclosure, a retinal prosthesis system capable of acquiring image information and stimulating the retina simultaneously and ensuring high resolution by integrating a nanowire photodetector and at least one micro electrode together on a flexible substrate, and a method for manufacturing the same may be provided.

Technical Solution

In one general aspect, there is provided a retinal prosthesis system, which may include: a flexible substrate; a nanowire photodetector located on the substrate and having at least one nanowire whose resistance varies according to an applied light; at least one micro electrode located on the substrate, electrically connected to the nanowire photodetector and contacting a retina cell; and a power source for applying an electric power to the nanowire photodetector and the micro electrode.

In an embodiment, the nanowire photodetector may modulate the electric power, applied by the power source, according to the applied light and transmit the modulated power to the at least one micro electrode. In addition, at least one micro electrode may apply the modulated power, transmitted from the nanowire photodetector, to the retina cell to stimulate the retina cell.

In another general aspect, there is provided a method for manufacturing a retinal prosthesis system, which may include: forming at least one nanowire, whose resistance varies according to an applied light, on a first substrate; forming at least one micro electrode on a second substrate; bonding the first substrate and the second substrate to each other; forming a nanowire photodetector by using the first substrate and the at least one nanowire; electrically connecting the nanowire photodetector and the at least one micro electrode; forming a support layer, made of flexible material, on the nanowire photodetector and the at least one micro electrode; and removing the second substrate.

In an embodiment, the forming of at least one nanowire may include: forming a dent region by partially etching the first substrate; forming a first oxide film on the first substrate including the dent region; removing the first oxide film located on a bottom surface of the dent region; forming at least one column structure, which includes a first portion having a first width and a second portion having a second width smaller than the first width and supporting the first portion, by etching the first substrate by using the first oxide film as an etching mask; removing the first oxide film; and forming a second oxide film on the first substrate including the column structure so that the first portion is not oxidized but surrounded by the second oxide film to include a region corresponding to the nanowire when the second oxide film is formed.

In an embodiment, the second substrate may include a third substrate and a fourth substrate bonded to each other. In addition, the forming of at least one micro electrode may include: forming at least one dent region by partially etching the third substrate; forming a plating base on the third substrate including the at least one dent region; bonding the fourth substrate on the third substrate including the plating base, the fourth substrate including at least one hole, so that each dent region is arranged with each hole; and forming a conductive material in each dent region and each hole.

Advantageous Effects

According to an aspect of the present disclosure, a retinal prosthesis system having a very thin and flexible substrate form may be provided by making a nanowire photodetector on a substrate where at least one micro electrode is formed. In addition, since the nanowire photodetector and the micro electrode may be fabricated in a single pixel, it is easy to manufacture a high-resolution retinal prosthesis system by means of high-density electrodes.

Moreover, since a nanowire may be used in the photodetector, the photodetector may be fabricated in a very simple way, without using a complicated process such as a complementary metal-oxide semiconductor (CMOS). In addition, a nanowire field effect transistor (FET) may be used to implement a signal amplification circuit diagram.

Further, the retinal prosthesis system may be transplanted to be closely adhered to the eyeball according to the curvature thereof since it is fabricated in a flexible substrate form. In addition, micro electrodes may be arranged in an array pattern, and each micro electrode may be configured as a 3D micro electrode. As a result, the micro electrode may contact the retina organization more firmly in comparison to a 2D electrode, and the contact area greatly increases. Therefore, the contact resistance between the micro electrode and the retina cell may be lowered, which is advantageous when transmitting a stimulation signal.

DESCRIPTION OF DRAWINGS

FIG. 3a is a diagram showing a retinal prosthesis system according to an embodiment.

FIG. 3b is a plane view showing a nanowire photodetector and a micro electrode array for one pixel, employed in the retinal prosthesis system of FIG. 3a.

BEST MODE

Figure 1:
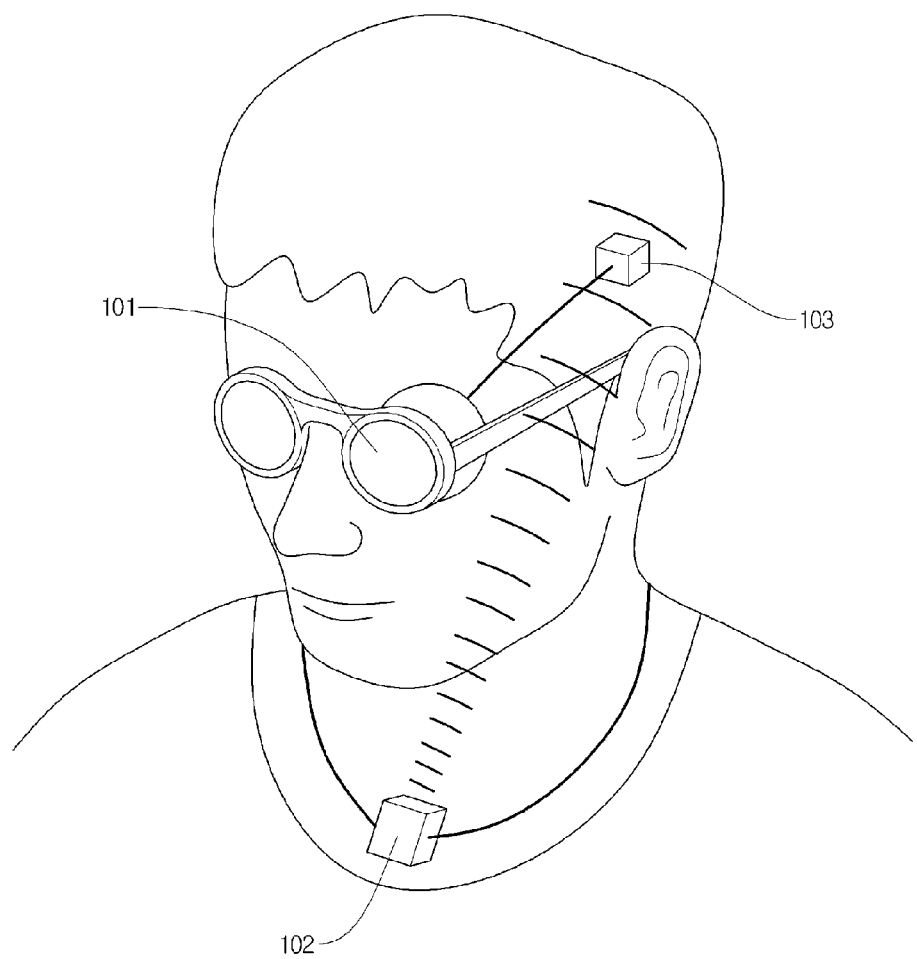
FIG. 1 shows an example of a general retinal prosthesis system not including an image sensor.
Figure 2:
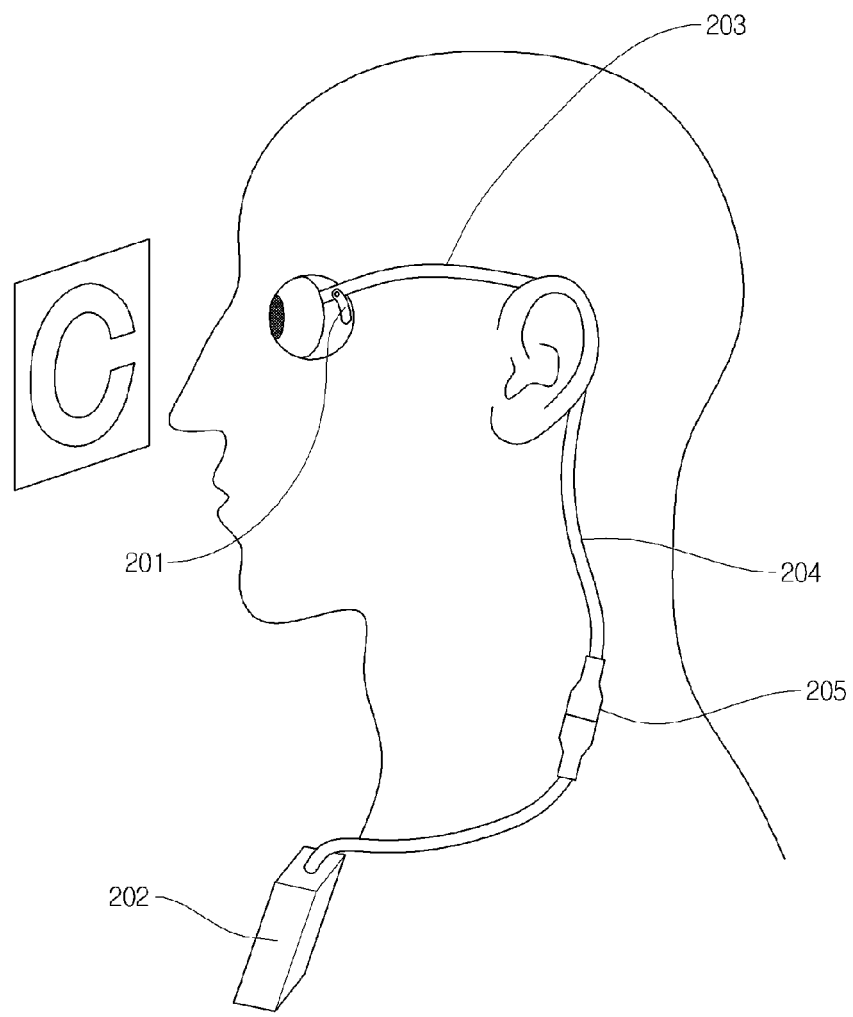
FIG. 2 shows an example of a general retinal prosthesis system including an image sensor.

Hereinafter, embodiments of the present disclosure will be described with reference to the drawings.

FIG. 3a is a diagram showing a retinal prosthesis system according to an embodiment. The retinal prosthesis system according to embodiments of the present disclosure includes a photodetector.

Referring to FIG. 3a, the retinal prosthesis system according to an embodiment may include a substrate 300, a nanowire photodetector 301, a micro electrode array 302 and a power source 303. In an embodiment, the nanowire photodetector 301 and the micro electrode array 302 may be integrated on the substrate 300 in an integral form. In addition, the substrate 300, the nanowire photodetector 301 and the micro electrode array 302 may be transplanted in a living body, for example in the eyeball. Meanwhile, the power source 303 may not be transplanted in the eyeball of a living body but located spaced apart therefrom. In other cases, the power source 303 may not be transplanted in a living body but located out of the living body.

The substrate 300 may be made of flexible material. As a result, if the substrate 300 and the nanowire photodetector 301 and the micro electrode array 302 formed on the substrate 300 are transplanted on the eyeball, they may be closely adhered to the eyeball according to a curvature of the eyeball. In addition, the substrate 300 may be made of material which may be patterned by means of photolithography and absorbs less moisture after high-temperature thermal treatment even though being exposed to moisture for a long time so that current is not easily leaked between electrodes and wires. For example, the substrate 300 may be a single or a multi layers made of polymer or polyimide, without being limited thereto.

The nanowire photodetector 301 is a component for acquiring image information. The nanowire photodetector 301 may include at least one nanowire whose resistance varies according to light. In an embodiment, each nanowire may be a silicon nanowire. The nanowire photodetector 301 may be electrically connected to the micro electrode array 302 and the power source 303. The nanowire photodetector 301 modulates a power signal from the power source 303 according to an applied light.

The micro electrode array 302 is a component for stimulating the retina cell according to the modulated power signal transmitted from the nanowire photodetector 301. The micro electrode array 302 may be located to at least partially contact the retina cell. The micro electrode array 302 may include a plurality of micro electrodes arranged in an array pattern, but it is just an example, and as another embodiment, the retinal prosthesis system may include at least one micro electrode arranged regularly or irregularly. In an embodiment, each micro electrode may be a 3D electrode. In other words, each micro electrode may be shaped to protrude in the vertical direction from the surface of the substrate 300. As a result, the contact area between the retina cell and the micro electrode increases, which may lower the contact resistance between the micro electrode and the retina cell.

The power source 303 is a component for supplying a power to the nanowire photodetector 301 and the micro electrode array 302 to stimulate the retina cell. In addition, the signal waveform for stimulating the retina may be generated at the power source 303. In an embodiment, the power source 303 may be fabricated as an independent element separate from the nanowire photodetector 301 and the micro electrode array 302. For example, the power source 303 may be fabricated in a chip form by means of a complementary metal-oxide semiconductor (CMOS) process or the like. For example, the power source 303 may include an application-specific integrated circuit (ASIC) chip which performs signal generation, logic operation or the like for stimulating the retina. In addition, the power source 303 may include a battery.

Figure 3B:
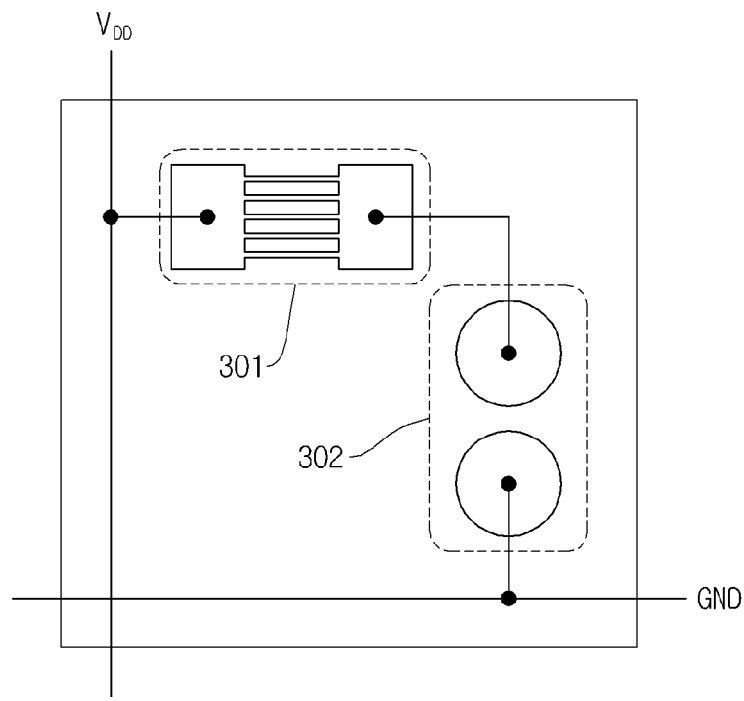
Figure 3C:
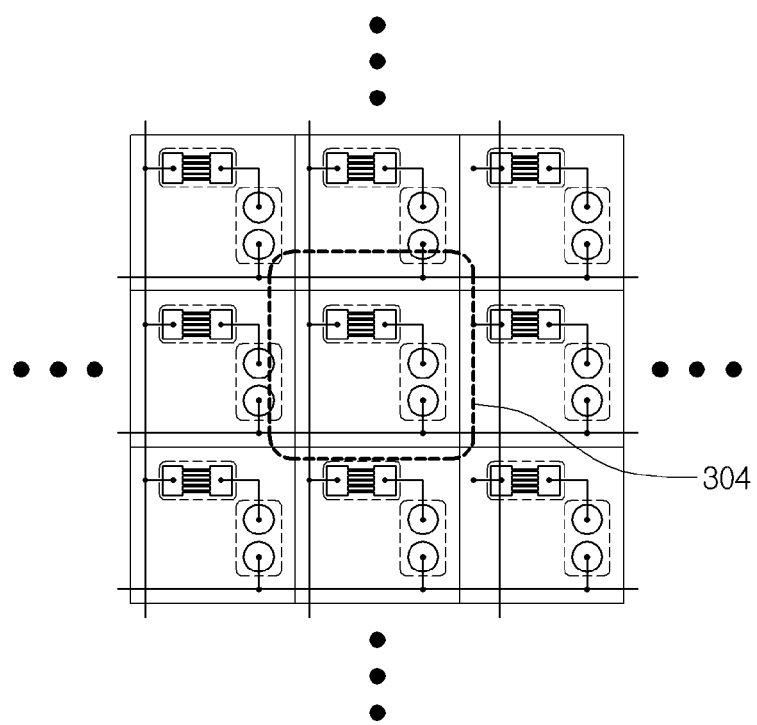
FIG. 3c is a diagram showing a pixel array in which unit pixels shown in FIG. 3b are arranged in an N×N matrix pattern.

FIG. 3b is a plane view showing a nanowire photodetector 301 and a micro electrode array 302 for one pixel, employed in the retinal prosthesis system of FIG. 3a, and FIG. 3c is a diagram showing a pixel array in which unit pixels shown in FIG. 3b are arranged in a N×N matrix pattern. As shown in the figures, the nanowire photodetector 301 and the micro electrode array 302 are provided in each unit pixel 304, and a high-resolution retinal prosthesis system may be implemented by repeatedly disposing such unit pixels 304 in a matrix pattern.

Figure 4:
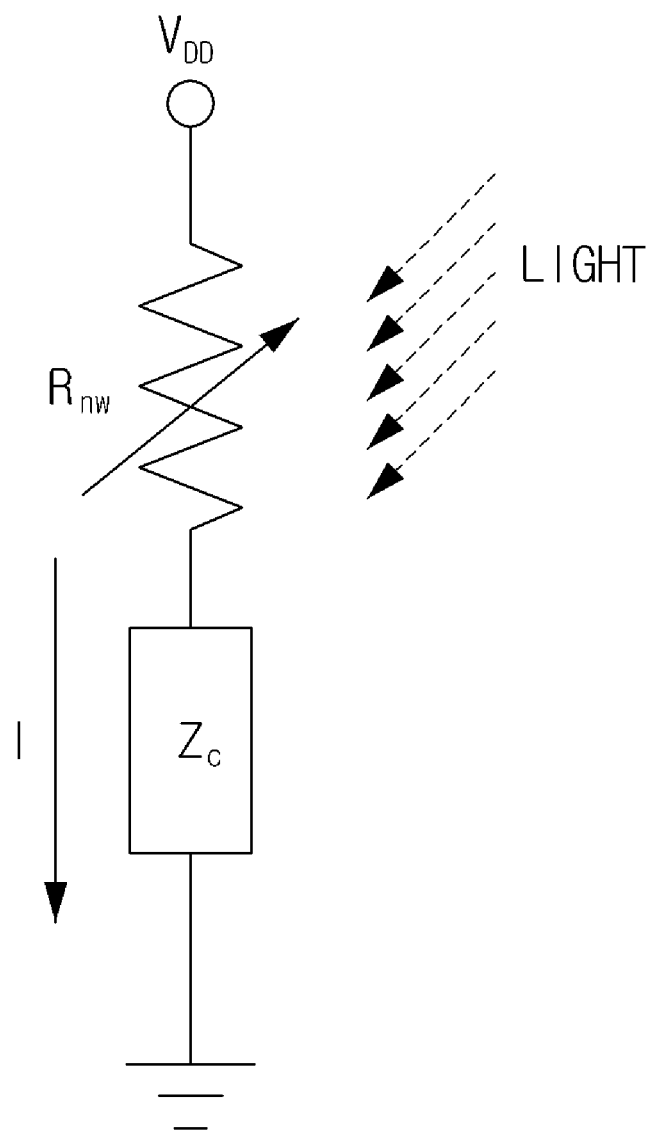
FIG. 4 is a circuit diagram showing an equivalent circuit of a unit pixel in the retinal prosthesis system according to an embodiment.

FIG. 4 is a circuit diagram showing an equivalent circuit of the nanowire photodetector and the micro electrode array of a unit pixel in the retinal prosthesis system according to an embodiment.

Referring to FIG. 4, the nanowire photodetector has a constant resistance value if light is not irradiated thereto. However, if light is irradiated, electron-hole pairs are generated in the nanowire. The electric resistance of the nanowire is lowered due to a plurality of increased carriers [for example, pores in case of a p-type silicon] among them. Therefore, the nanowire photodetector may be expressed as a kind of variable resistor $R_{nw}$ whose resistance varies according to the intensity of light. Meanwhile, the micro electrode array may be expressed as a characteristic impedance $Z_c$, and the value of the characteristic impedance $Z_c$ may be determined based on a contact impedance between the micro electrode array and the retina cell organization and an intrinsic impedance of the retina organization. In such an equivalent circuit, the intensity of current I flowing through the micro electrode array is determined in inverse proportion to the intensity of the characteristic impedance $Z_c$.

The intensity of the variable resistor $R_{nw}$ corresponding to the nanowire photodetector may be assumed as being greatly high in comparison to the intensity of the characteristic impedance $Z_c$ of the micro electrode array and the retina cell organization. At this time, the power source $V_{DD}$ plays a role of generating a stimulation signal waveform for stimulating the retina cell, and the nanowire photodetector plays a role of modulating the signal, generated from the power source, according to the intensity of external light. In addition, the micro electrode array plays roles of receiving the signal modulated by the nanowire photodetector and transmitting the modulated signal to the retina cell to stimulate the retina.

FIGS. 5a to 5e are graphs showing a waveform of power, an incident light and a waveform of a retina stimulation signal at the retinal prosthesis system according to an embodiment.

Figure 5A:
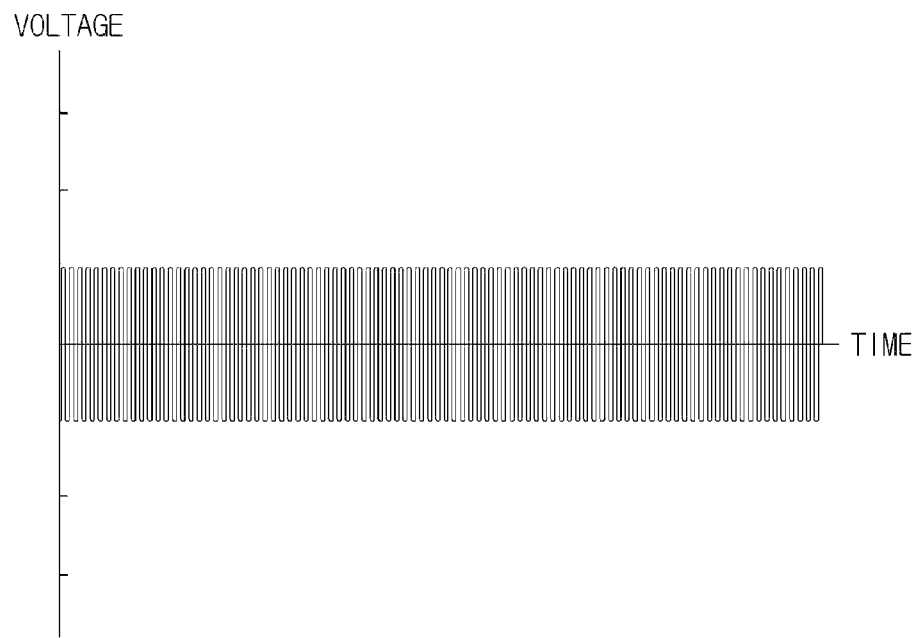
FIGS. 5a to 5e are graphs showing a waveform of power, an incident light and a waveform of a retina stimulation signal at the retinal prosthesis system according to an embodiment.

FIG. 5a shows a waveform of a power generated by the power source. As shown in FIG. 5a, the power source may apply a pulse-type signal with predetermined intensity and frequency. The pulse signal may be a signal optimized to effectively stimulate the retina cell. However, it is just an example, and the form of a signal applied by the power source is not limited to a pulse form.

Figure 5B:
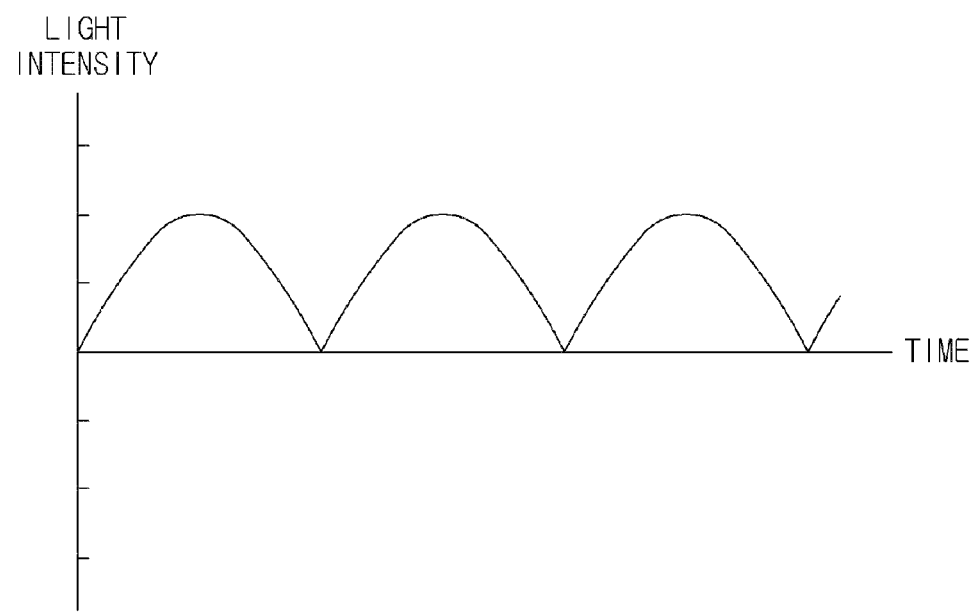
Figure 5C:
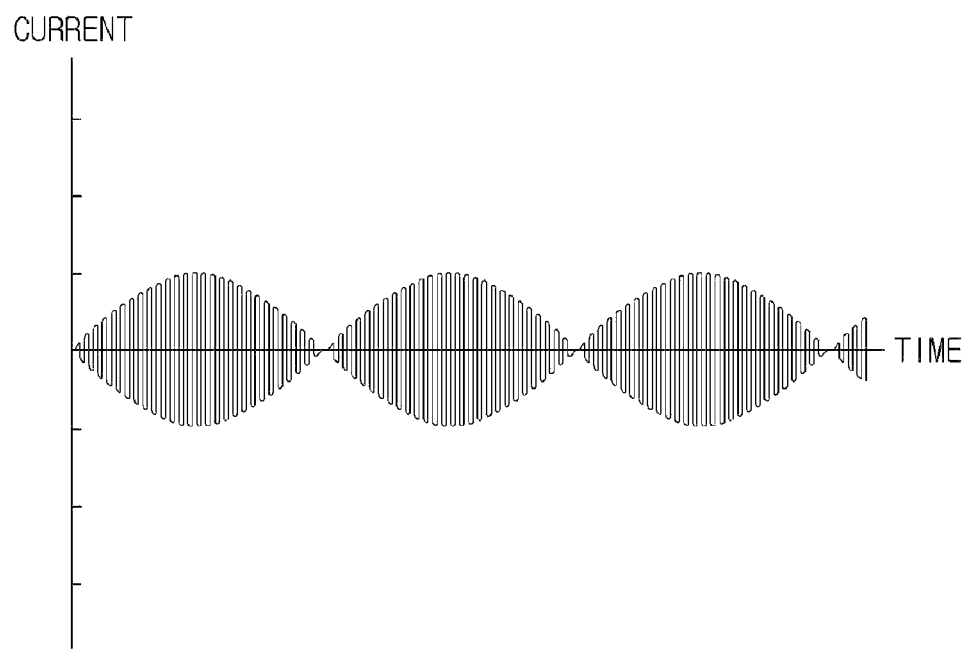

FIG. 5b shows an incident light of a sine wave, which may be applied to the retinal prosthesis system according to an embodiment. In addition, FIG. 5c shows a current waveform flowing through the micro electrode array when the power waveform as shown in FIG. 5a and the incident light as shown in FIG. 5b are applied. Since the resistance of the nanowire photodetector varies according to the intensity of light, the current as shown in FIG. 5c flows through the micro electrode array.

Figure 5D:
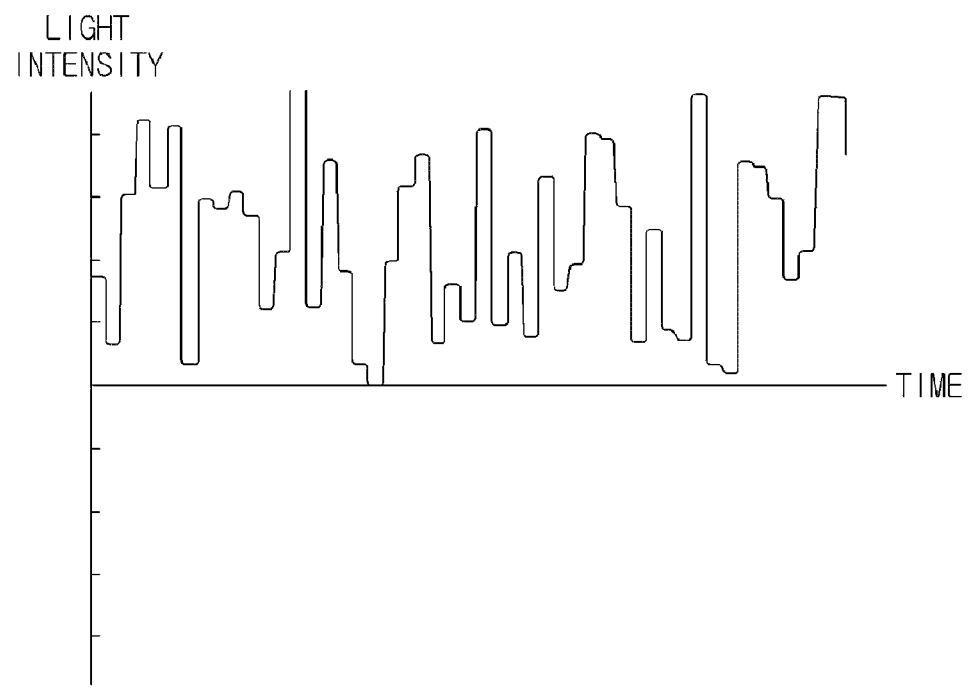
Figure 5E:
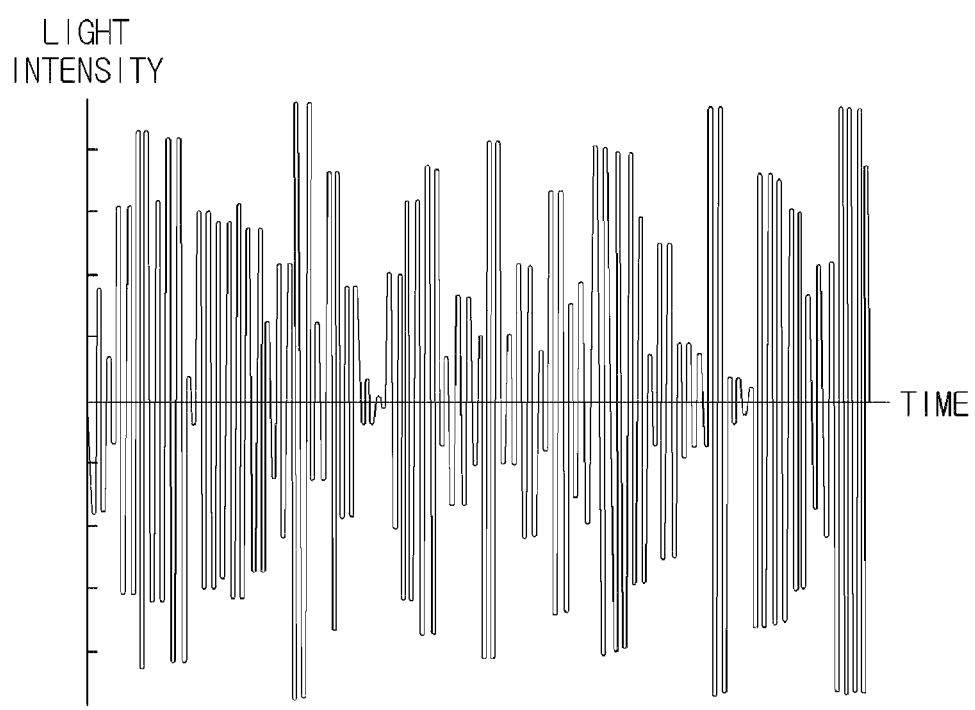

FIG. 5d shows an incident light of a random shape, which is another example of an incident light which may be applied to the retinal prosthesis system according to an embodiment. In addition, FIG. 5e shows a waveform of current flowing through the micro electrode array when a power waveform as shown in FIG. 5a and an incident light as shown in FIG. 5d are applied.

Hereinafter, a method for manufacturing a retinal prosthesis system according to an embodiment will be described.

Figure 6:
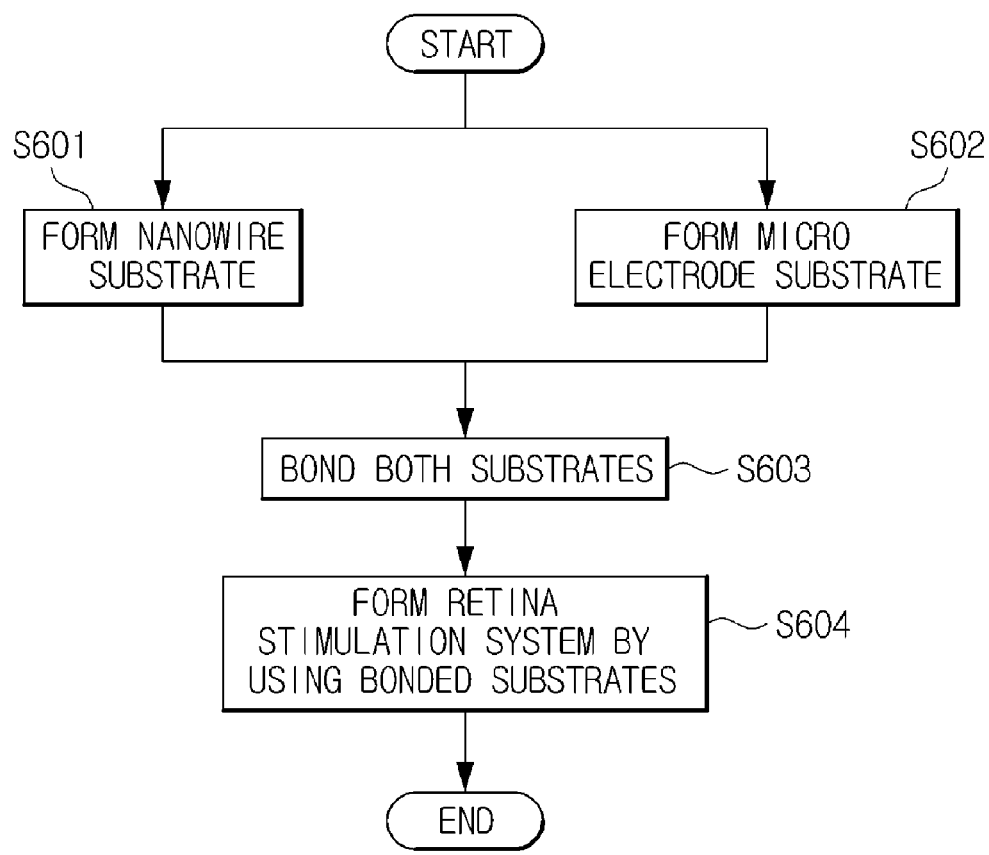
FIG. 6 is a flowchart for illustrating a method for manufacturing a retinal prosthesis system according to an embodiment.

FIG. 6 is a flowchart for illustrating a method for manufacturing a retinal prosthesis system according to an embodiment.

Referring to FIG. 6, the method for manufacturing a retinal prosthesis system may includes forming a nanowire substrate (S601) and forming a micro electrode substrate (S602). At least one nanowire may be formed on the nanowire substrate. In addition, at least one micro electrode, for example a micro electrode array, may be formed on the micro electrode substrate. Moreover, the method for manufacturing a retinal prosthesis system may include bonding the nanowire substrate and the micro electrode substrate (S603).

Further, the method for manufacturing a retinal prosthesis system may include forming a retina stimulation system by using two bonded substrates (S604). S604 may include forming a nanowire photodetector and an electrode wire by etching silicon, forming a metal electrode, forming a polymer substrate or the like by using the bonded substrates. In addition, S604 may include mounting a power source prepared as a separate chip on the substrate. Each operation shown in FIG. 6 will be described below in detail.

FIGS. 7a to 7j are diagrams showing a nanowire substrate making operation in the method for manufacturing a retinal prosthesis system according to an embodiment.

Figure 7A:
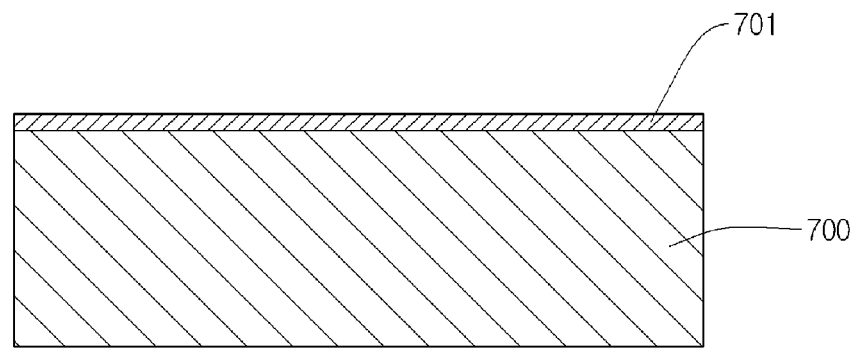
FIGS. 7a to 7j are diagrams showing a nanowire substrate making operation in the method for manufacturing a retinal prosthesis system according to an embodiment.

Referring to FIG. 7a, a substrate 700 may be prepared, and an oxide film 701 may be formed on the substrate 700. For example, the substrate 700 may be made of silicon, and the oxide film 701 may be made of silicon oxide ($SiO_2$). At this time, the substrate 700 may use a silicon substrate whose upper surface has a crystal direction of (111), without being limited thereto.

Figure 7B:
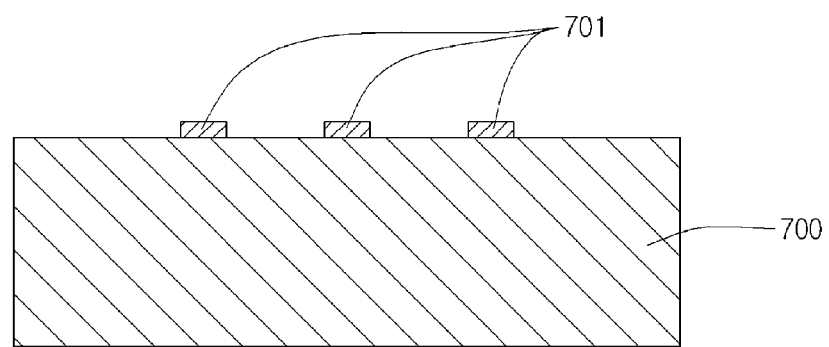

Referring to FIG. 7b, the formed oxide film 701 may be patterned into a predetermined shape. The oxide film 701 may be patterned by means of photolithography, dry-etching or other suitable processes.

Figure 7C:
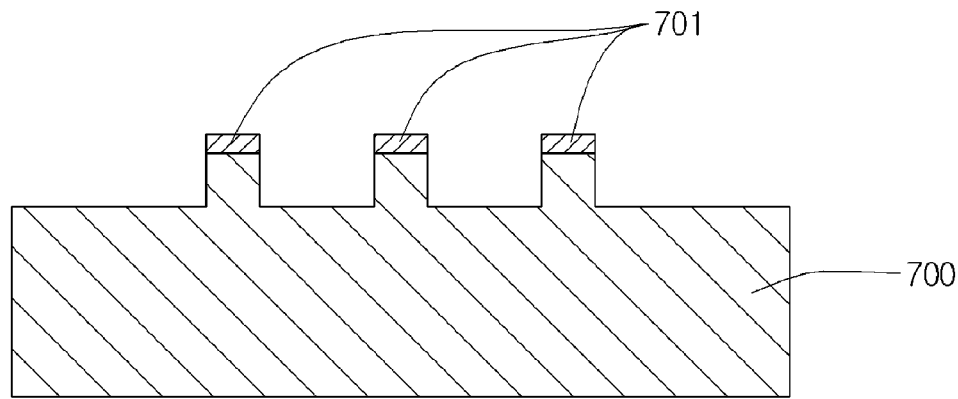

Referring to FIG. 7c, the substrate 700 may be etched to a predetermined depth by using the patterned oxide film 701 as an etching mask. As a result, a surface region of the substrate 700, which is not be covered by the oxide film 701 but exposed, is etched to form a dent region. The substrate 700 may be dry-etched, without being limited thereto.

Figure 7D:
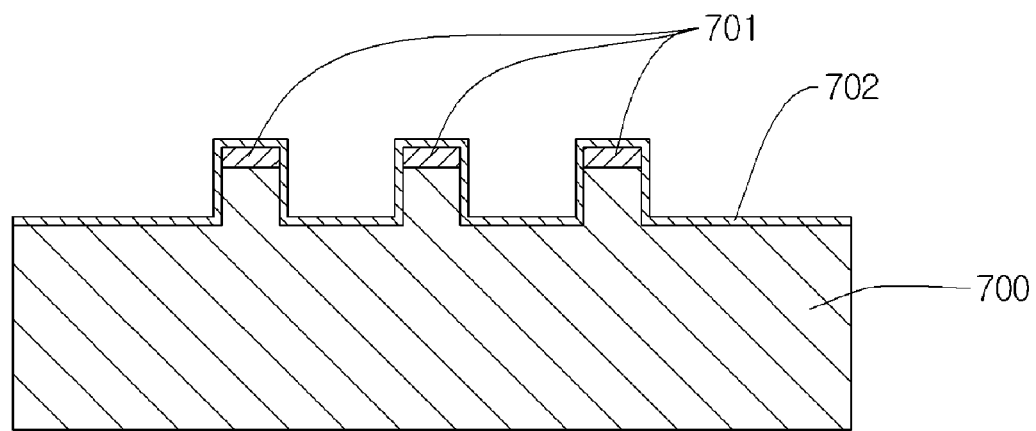

Referring to FIG. 7d, after the substrate 700 is etched, an oxide film 702 may be formed again on the surface of the substrate 700. For example, the oxide film 702 may be deposited in a predetermined thickness by means of chemical vapor deposition (CVD), without being limited thereto.

Figure 7E:
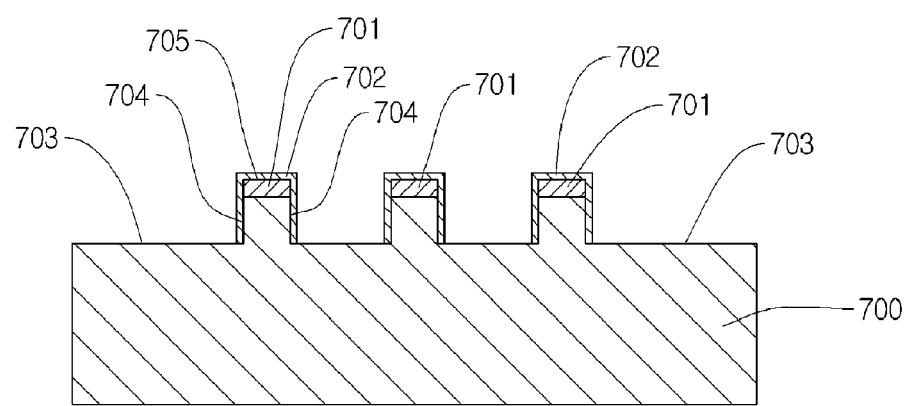

Referring to FIG. 7e, the oxide film 702 located at a bottom surface 703 of the dent region formed at the surface of the substrate 700 by etching may be removed. For example, the oxide film 702 may be removed by means of dry-etching, without being limited thereto. If the oxide film 702 is selectively removed as described above, the oxide film 702 may remain only on a vertical surface 704 of the dent region of the substrate 700 and an upper surface 705 of the substrate 700 not etched.

Figure 7F:
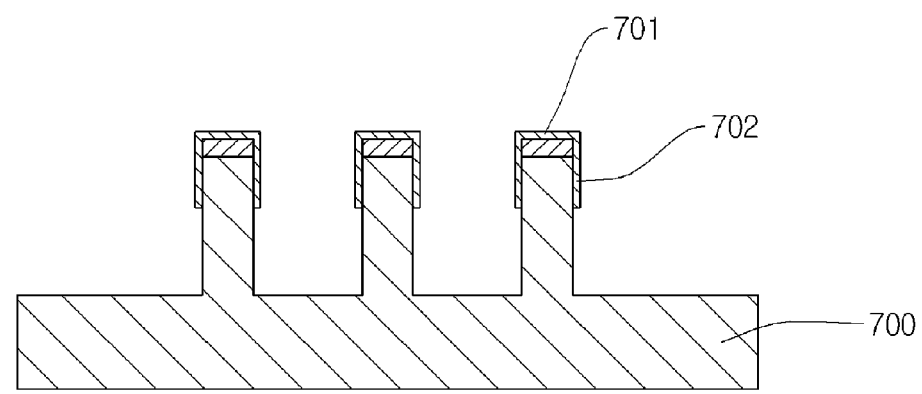

Referring to FIG. 7f, the substrate 700 may be additionally etched by using the oxide film 702 located on the vertical surface of the dent region of the substrate 700 and the upper surface of the substrate 700 as an etching mask. For example, the substrate 700 may be dry-etched, without being limited thereto.

Figure 7G:
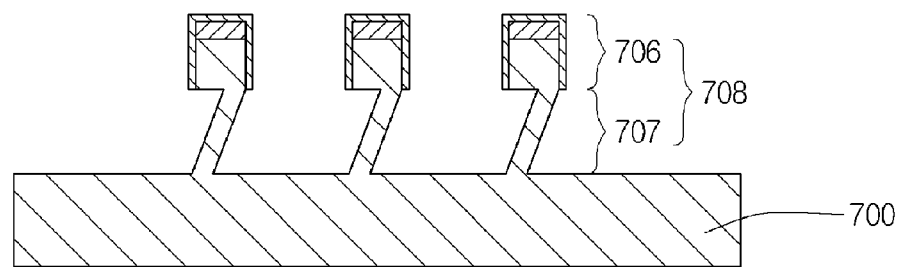

Referring to FIG. 7g, the region of the substrate 700 exposed during the above etching process may be additionally wet-etched to form a column structure 708 including a first portion 706 and a second portion 707 supporting the first portion 706. In the column structure 708, the first portion 706 may be a portion having a relatively greater width, and the second portion 707 may be a portion having a relatively smaller width and supporting the first portion 706. As a result of the wet etching, the second portion 707 may extend with a slope with respect to the surface of the substrate 700. When the column structure 708 is formed, the substrate 700 may be wet-etched by using a tetra-methyl-ammonium-hydroxide (TMAH) solution, a potassium hydroxide (KOH) solution or other suitable materials, without being limited thereto.

Figure 7H:
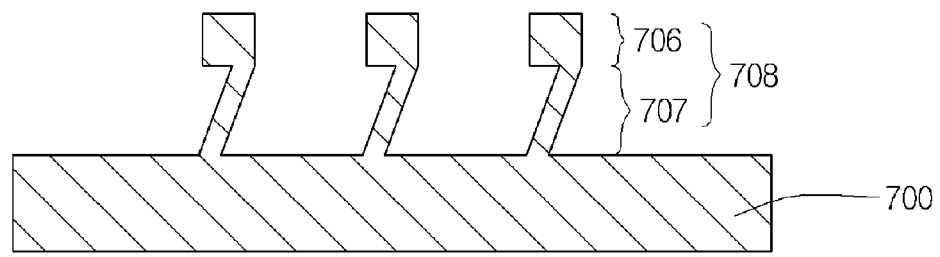

Referring to FIG. 7h, the oxide film partially covering the upper and side surfaces of the formed column structure 708 may be removed. For example, the oxide film may be removed by using a hydrofluoric acid (HF) solution, without being limited thereto.

Figure 7I:
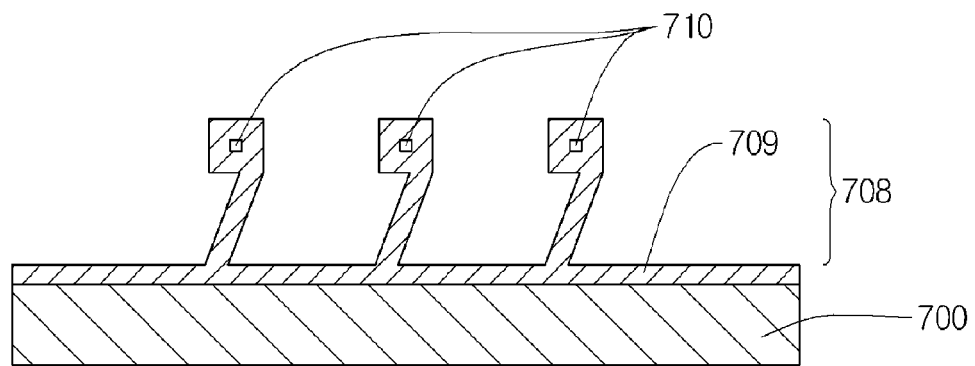

Referring to FIG. 7i, an oxide film 709 may be formed on the front surface of the substrate 700 by means of a wet-etching oxide film forming process. At this time, the thickness of the oxide film 709 may be suitably determined so that in the column structure 708, the first portion 706 having a relatively greater width may include an area 710 partially not covered by the oxide film 709 but exposed. If the exposed area 710 is electrically connected to another device, the column structure may play a role of a nanowire.

Figure 7J:
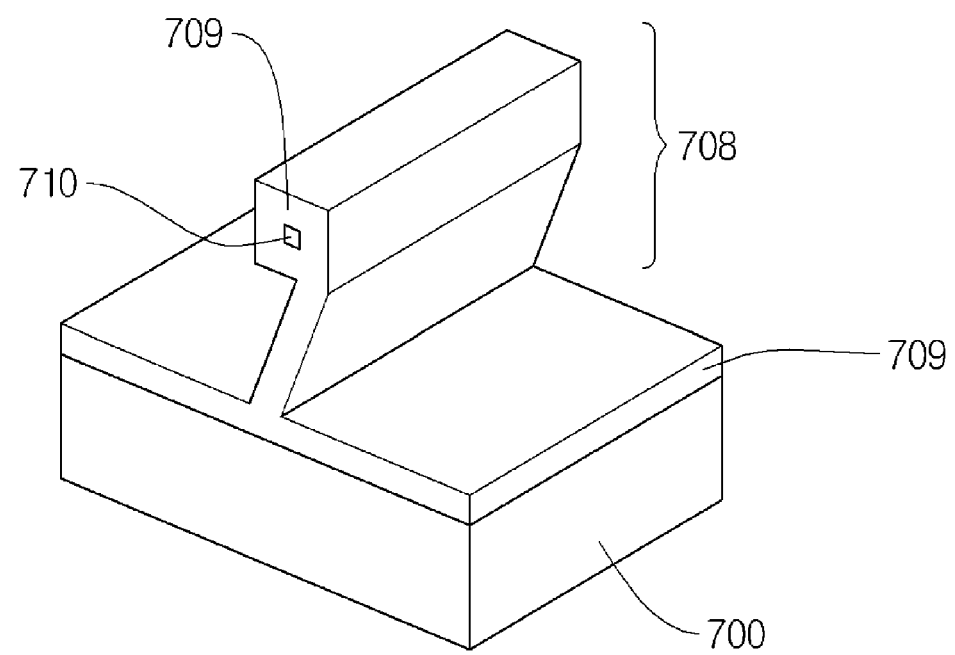

FIG. 7j is a perspective view showing a single column structure 708 shown in the cross-sectional view of FIG. 7i. Referring to FIGS. 7i and 7j, the column structure 708 is shaped to extend in one direction, and FIG. 7i shows a cross section in a direction perpendicular to the longitudinal direction of the column structure 708. Meanwhile, the column structure 708 includes the area 710 not covered by the oxide film 709 but exposed. If the exposed area 710 is electrically connected to the outside, current may flow through the column structure 708, so that the column structure 708 may play a role of a nanowire as a whole.

By using the procedures described above, the column structure 708 including at least one nanowire may be fabricated. The thickness of the nanowire fabricated as above may be determined at least partially based on the width of the column structure 708 fabricated through dry-etching and wet-etching as described above, thickness of the oxide film 709 formed by the wet-etching oxide film forming process to surround the nanowire or the like.

FIGS. 8a to 8i are diagrams showing a micro electrode substrate making operation in the method for manufacturing a retinal prosthesis system according to an embodiment.

Figure 8A:
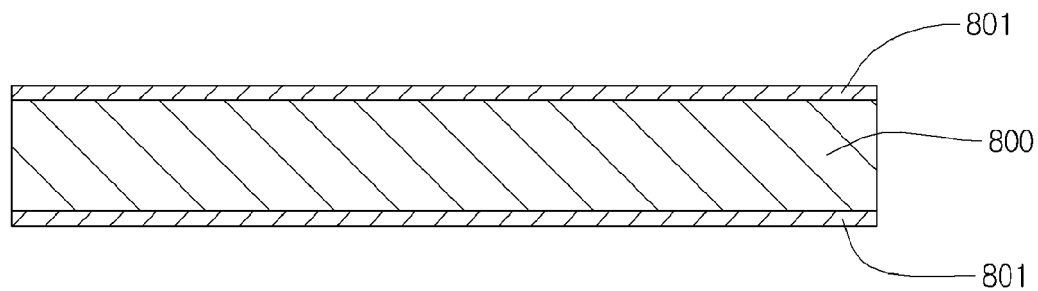
FIGS. 8a to 8i are diagrams showing a micro electrode substrate making operation in the method for manufacturing a retinal prosthesis system according to an embodiment.

Referring to FIG. 8a, a substrate 800 may be prepared, and an oxide film 801 may be formed on the substrate 800. For example, the substrate 800 may be made of silicon, and the oxide film 801 may be made of silicon oxide ($SiO_2$). The substrate 800 may employ a silicon substrate whose upper surface has a crystal direction of (100), without being limited thereto.

Figure 8B:
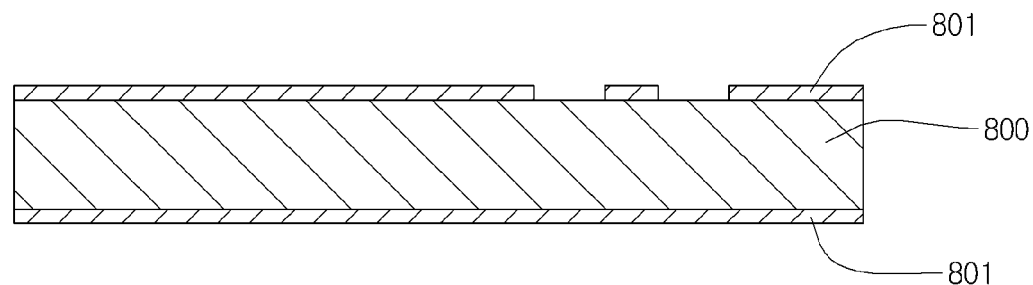

Referring to FIG. 8b, the oxide film 801 may be patterned into a predetermined shape, so that an area partially not covered by the oxide film 801 but exposed may be formed on the substrate 800. The oxide film 801 may be patterned by means of photolithography, dry-etching or other suitable processes.

Figure 8C:
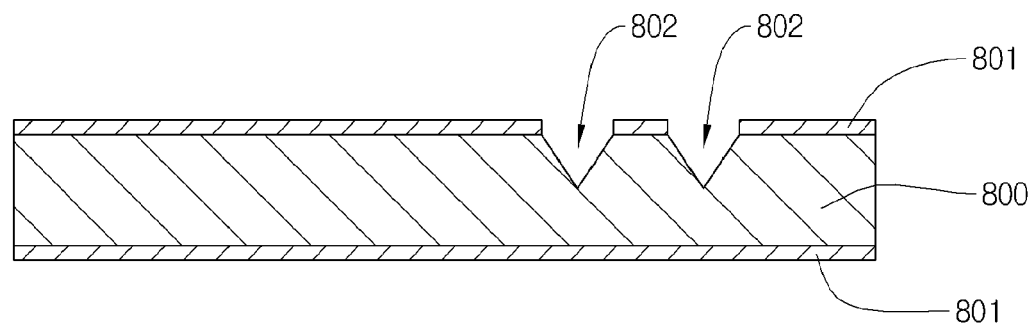

Referring to FIG. 8c, the substrate 800 may be etched by using the patterned oxide film 801 as an etching mask. For example, the substrate 800 may be wet-etched by using a TMAH solution or a potassium hydroxide solution, without being limited thereto. If the substrate 800 is etched, at least one dent region 802 may be formed in the substrate 800. For example, each dent region 802 may be formed with a concave quadrangular pyramid shape.

Figure 8D:
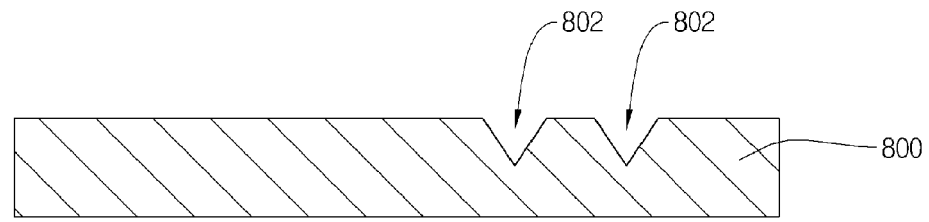

Referring to FIG. 8d, after the dent region 802 is formed by etching the substrate 800, the oxide film 801 may be removed.

Figure 8E:
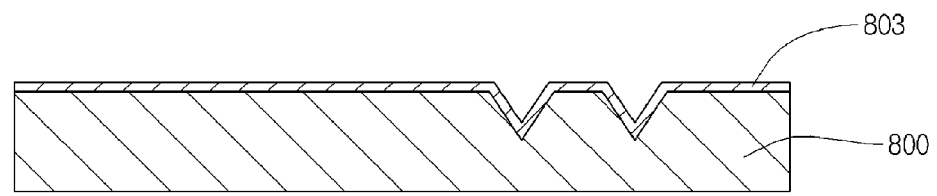

Referring to FIG. 8e, a plating base 803 for electroforming may be formed on the substrate 800. The plating base 803 may be made of titanium (Ti), gold (Au) or other suitable conductive material. In addition, the plating base 803 may have a single layer structure or a multi layer structure made of a plurality of materials different from each other.

Figure 8F:
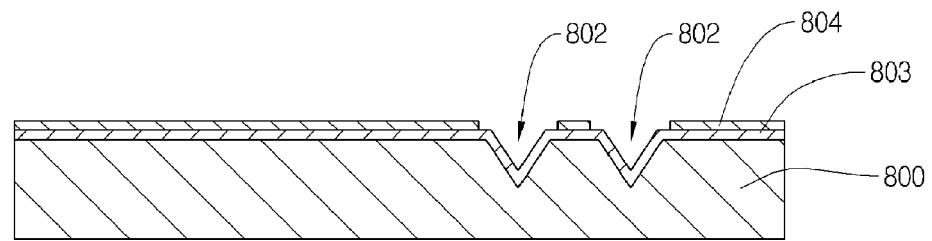

Referring to FIG. 8f, an adhesive material 804 may be applied onto the substrate 800 coated with the plating base 803. For example, the adhesive material 804 may be benzocyclobutene (BCB) or other suitable material. Next, the adhesive material 804 in a portion other than an adhesive surface may be removed. In other words, the adhesive material 804 may remain only on the upper surface of the substrate 800 other than the dent region 802.

Figure 8G:
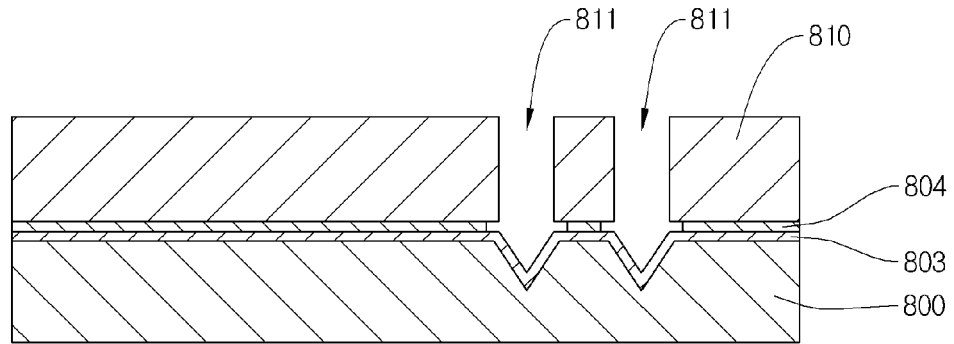

Referring to FIG. 8g, another substrate 810 may be adhered onto the substrate 800 on which the adhesive material 804 is formed. At least one hole 811 may be formed in the substrate 810 adhered. The at least one hole 811 may be formed through the substrate 810, and each hole 811 may be aligned with the dent region of the substrate 800.

Figure 8H:
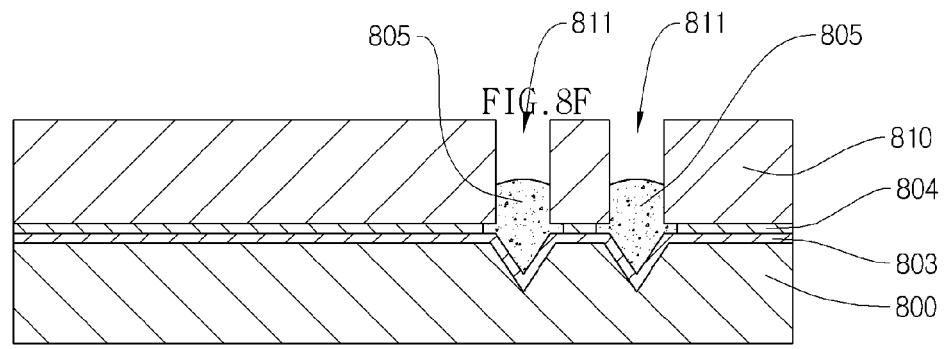

Referring to FIG. 8h, after two substrates 800, 810 are bonded, a conductive material 805 may be formed in the hole 811. For example, the conductive material 805 may be metal. The conductive material 805 may fill the hole 811 by means of electroforming. The conductive material 805 may also fill the dent region formed in the substrate 800 and may be formed according to the shape of the dent region. For example, an end portion of the conductive material 805 may have a quadrangular pyramid shape according to the shape of the dent region.

Figure 8I:
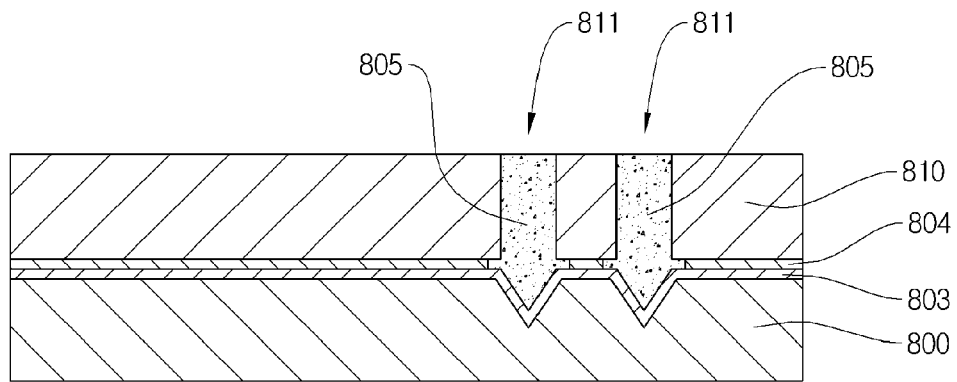

Referring to FIG. 8i, the hole 811 may be entirely filled with the conductive material 805. The conductive material 805 formed as above corresponds to at least one micro electrode in a retinal prosthesis system finally fabricated. In an embodiment, after the conductive material 805 entirely fills the hole 811, a process of polishing the upper surface of the substrate 810 may be further performed.

Figure 9A:
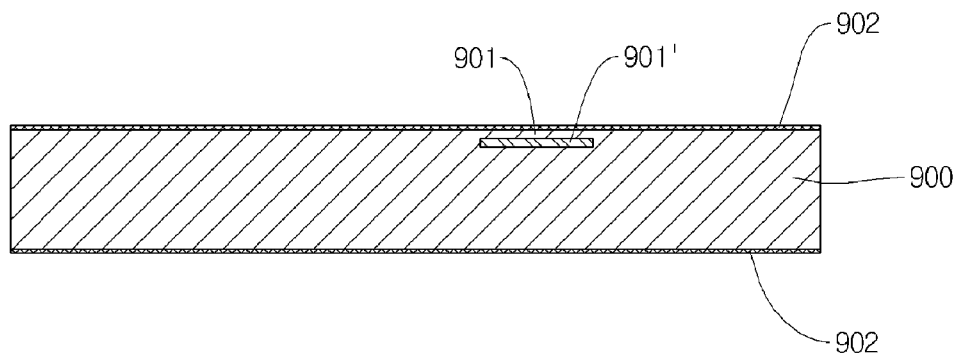
FIGS. 9a to 9p are diagrams showing an operation of completely manufacturing the retinal prosthesis system by bonding of the nanowire substrate and the micro electrode substrate and follow-up processes, in the method for manufacturing a retinal prosthesis system according to an embodiment.
Figure 9B:
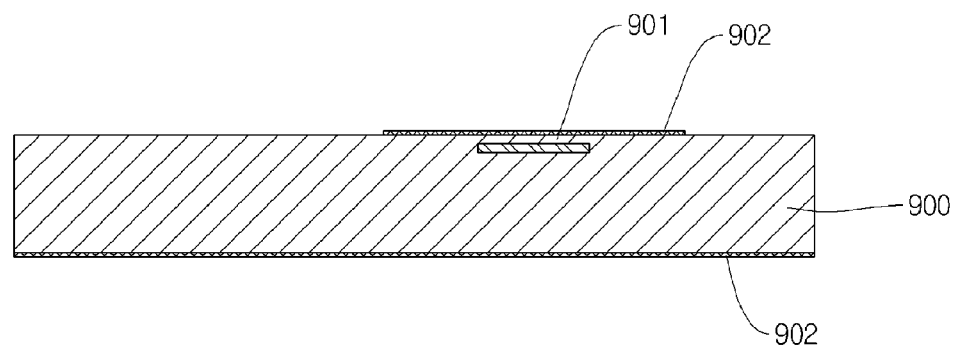
Figure 9C:
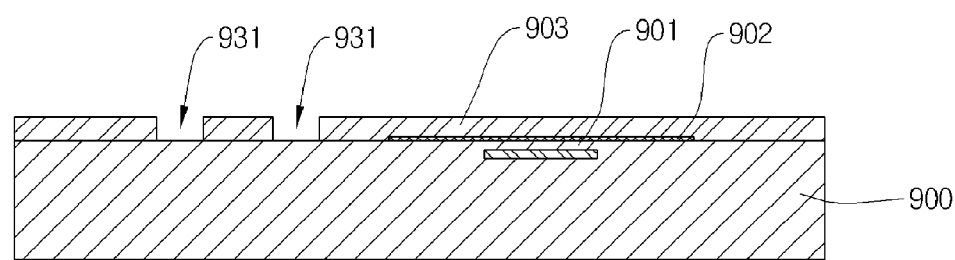
Figure 9D:
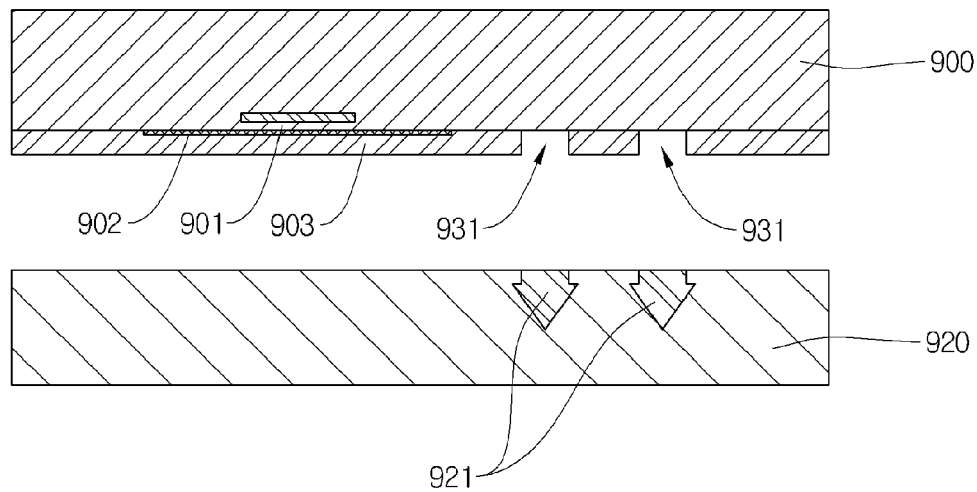
Figure 9E:
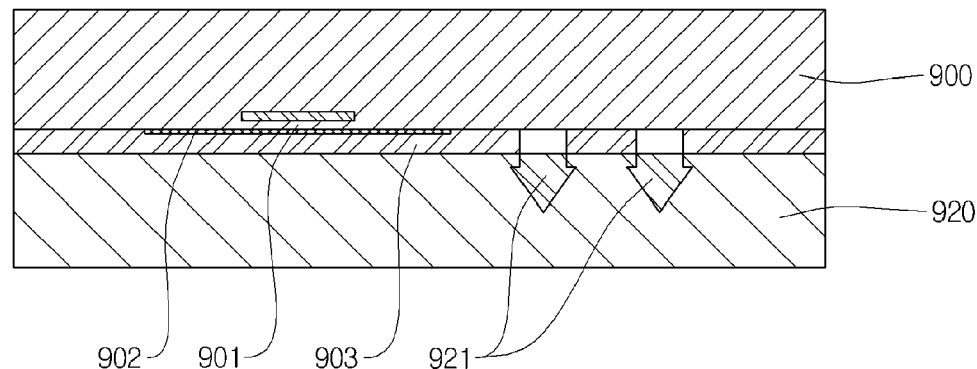
Figure 9F:
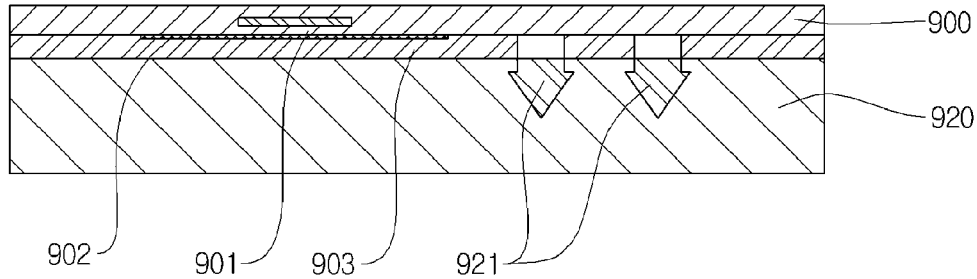
Figure 9G:
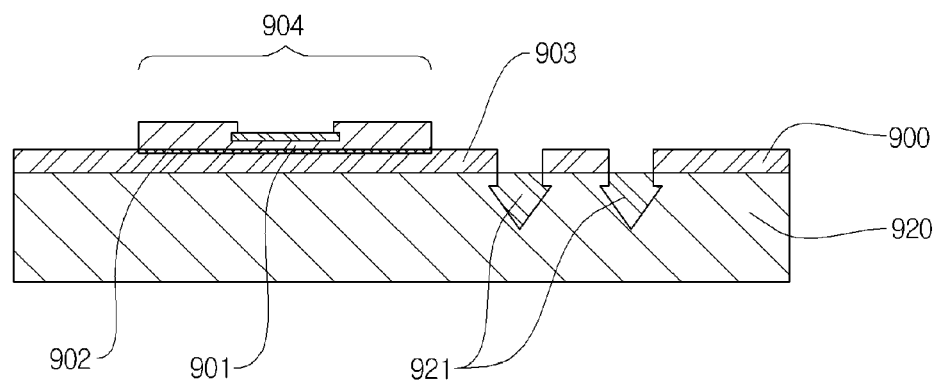
Figure 9H:
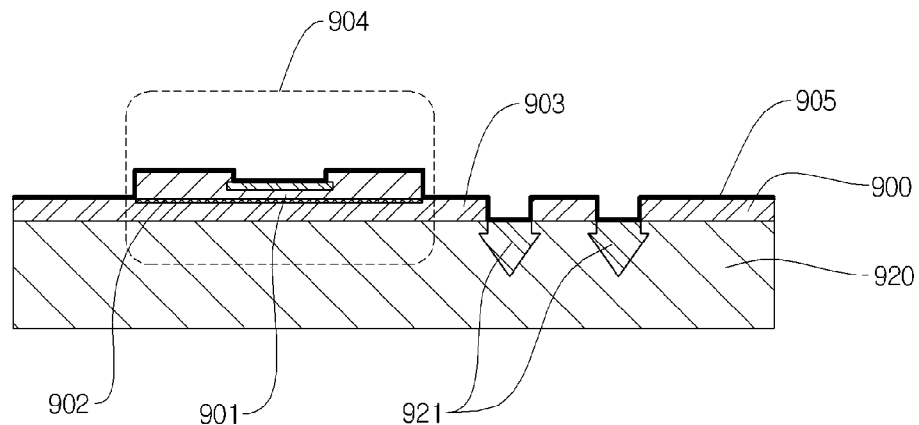
Figure 9I:
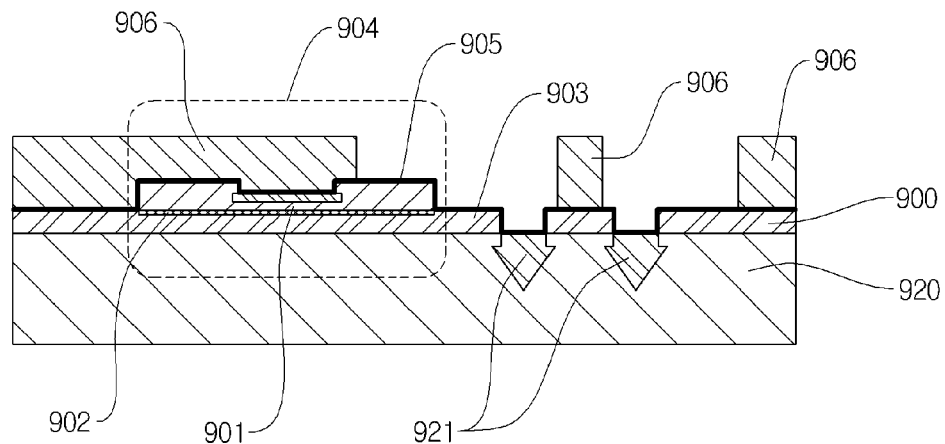
Figure 9J:
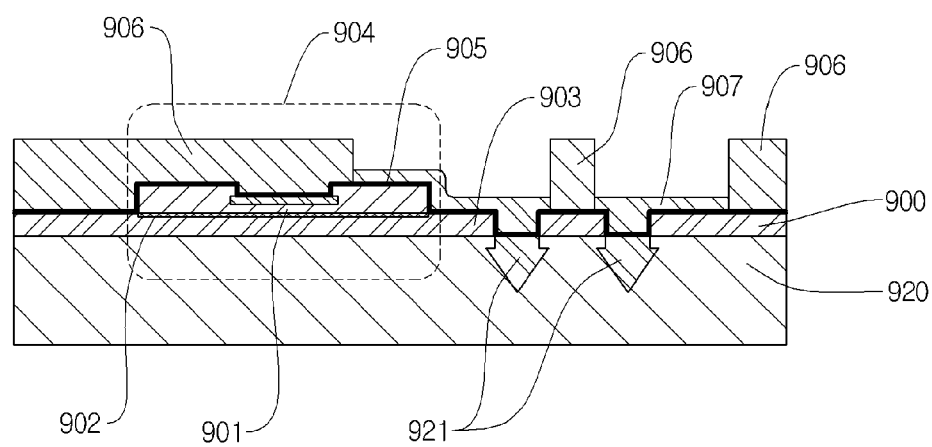
Figure 9K:
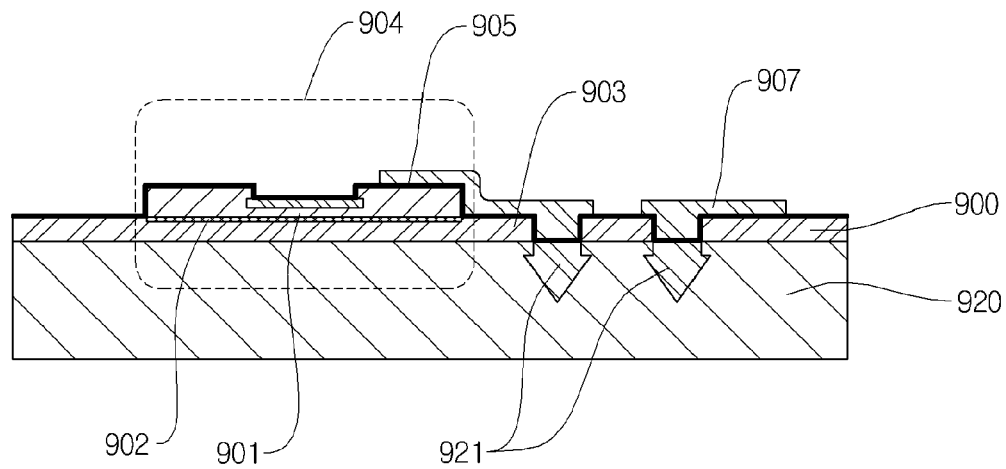
Figure 9L:
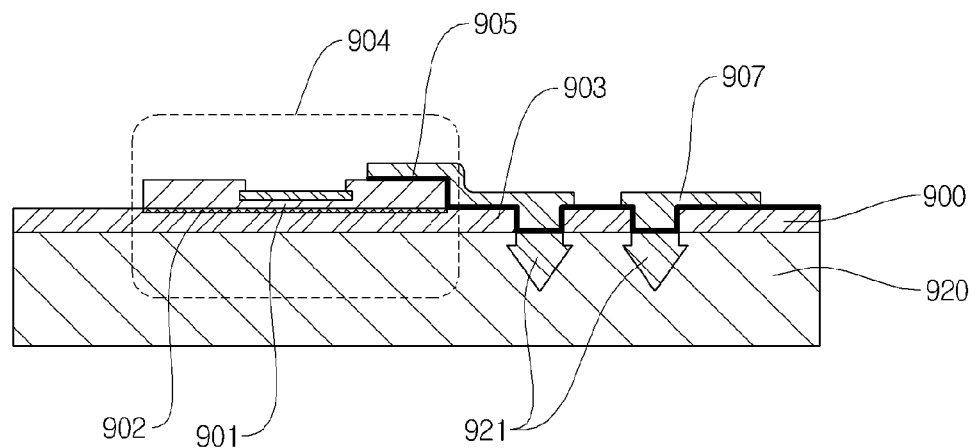
Figure 9M:
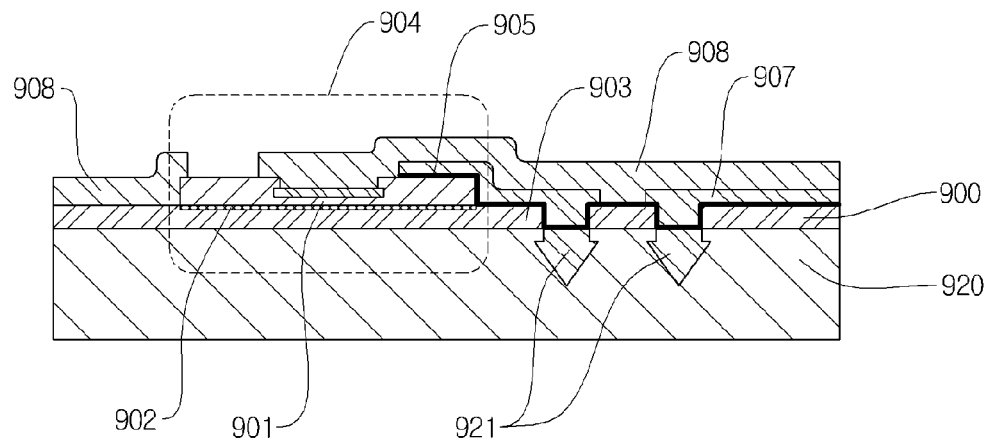
Figure 9N:
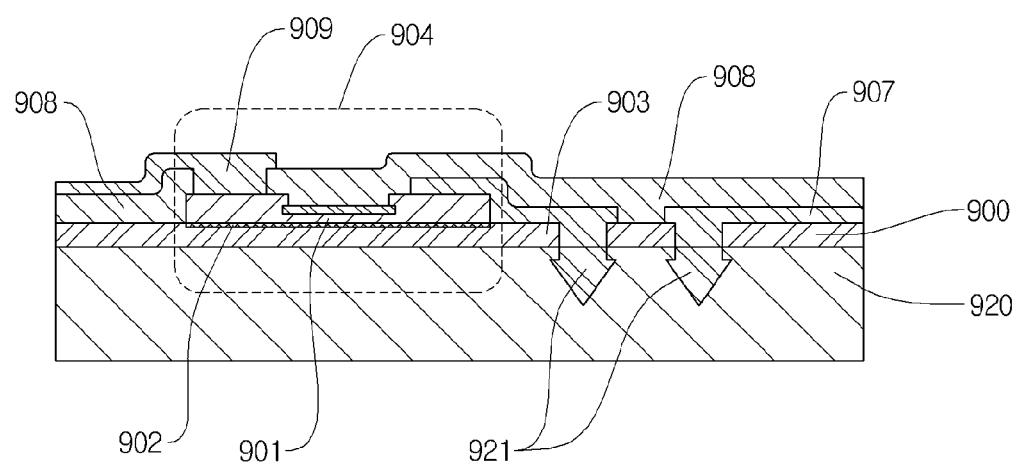
Figure 9O:
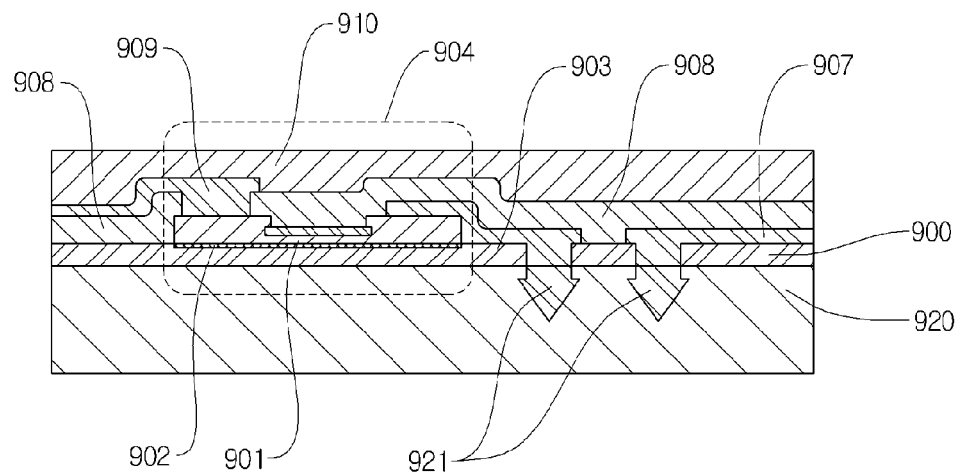
Figure 9P:
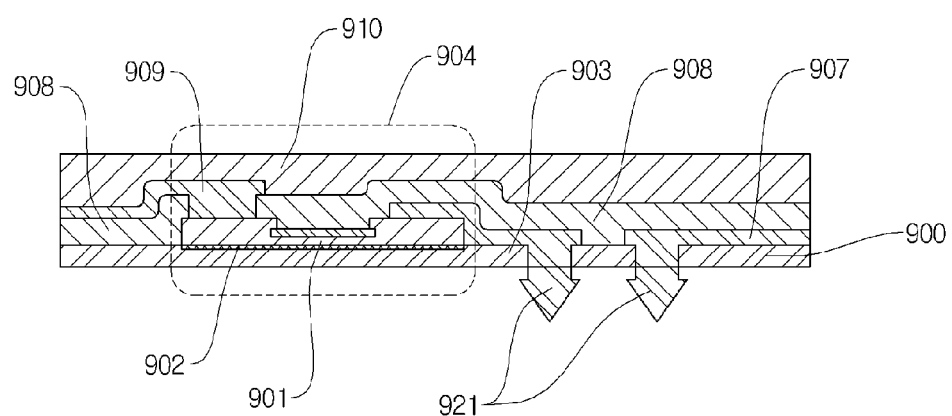

FIGS. 9a to 9p are diagrams showing an operation of completely manufacturing the retinal prosthesis system by bonding of the nanowire substrate and the micro electrode substrate and follow-up processes, in the method for manufacturing a retinal prosthesis system according to an embodiment.

Referring to FIG. 9a, a nanowire substrate 900 may be prepared. At least one nanowire 901 may be formed in the nanowire substrate 900. In an embodiment, the nanowire substrate 900 may be prepared according to the above method with reference to FIGS. 7a to 7j. In other words, at least one nanowire 901 may be surrounded by an oxide film 901' in a column structure including a first portion and a second portion, as described above with reference to FIGS. 7i and 7j. The detailed shape the column structure may be easily understood from the former embodiment and not described in detail again.

In FIGS. 9a to 9p, a component indicated by a reference symbol 901 corresponds to the at least one nanowire, and a person having ordinary skill in the art will easily understand that at least one nanowire 901 depicted in the figure does not represent actual shape, thickness and number of nanowire. If the nanowire substrate 900 including at least one nanowire 901 is prepared, an oxide film 902 may be formed on the nanowire substrate 900.

Referring to FIG. 9b, the oxide film 902 on the upper surface of the nanowire substrate 900 may be partially removed. For example, the oxide film 902 may be removed by means of photolithograph or the like, without being limited thereto. As a result, the oxide film 902 may remain only on a region where at least one nanowire 901 is formed.

Referring to FIG. 9c, an adhesive material 903 may be formed on an upper portion of the nanowire substrate 900. In addition, the adhesive material 903 may be patterned into a predetermined shape to form at least one hole 931 in the adhesive material 903. For example, the adhesive material 903 may be made of a BCB or the like, which may be patterned by means of photolithography, without being limited thereto.

Referring to FIG. 9d, a micro electrode substrate 920 may be aligned on the nanowire substrate 900. In an embodiment, the micro electrode substrate 920 may be prepared according to the above process described with reference to FIGS. 8a to 8i. The micro electrode substrate 920 includes at least one micro electrode 921, and may be located at the nanowire substrate 900 to face the surface where the adhesive material 903 is formed. At least one micro electrode 921 may be respectively aligned with the hole 931 formed in the adhesive material 903.

Referring to FIG. 9e, the nanowire substrate 900 and the micro electrode substrate 920 may be bonded by applying heat and/or pressure.

Referring to FIG. 9f, after the nanowire substrate 900 and the micro electrode substrate 920 are bonded, the nanowire substrate 900 may be polished into a predetermined thickness by means of thinning.

Referring to FIG. 9g, a nanowire photodetector 904 may be formed by using the nanowire substrate 900 polished into a predetermined thickness and the nanowire 901. The nanowire photodetector 904 may be obtained by forming electrodes and wires by means of photolithography, dry-etching or other suitable processes, in addition to at least one nanowire 901 formed at the nanowire substrate 900.

Referring to FIG. 9h, after the nanowire photodetector 904 is formed, a plating base 905 for electroforming may be formed on the nanowire substrate 900 and the micro electrode substrate 920 bonded to each other.

Referring to FIG. 9i, the nanowire substrate 900 and the micro electrode substrate 920 coated with the plating base 905 may also be coated with a photoresist film 906. Next, the photoresist film 906 may be partially removed by patterning. As a result, the plating base 905 located on a part of the nanowire photodetector 904 and at least one micro electrode 921 may be not covered by the photoresist film 906 but exposed out.

Referring to FIG. 9j, a conductive material 907 for forming an electrode may be formed on the plating base 905 which is not covered by the photoresist film 906 but exposed. For example, the conductive material 907 may be metal. The nanowire 901 of the nanowire photodetector 904 may be electrically connected to the conductive material 907. In addition, since the conductive material 907 is formed on the nanowire photodetector 904 and each micro electrode 921, the nanowire photodetector 904 and at least one micro electrode 921 may be electrically connected. In other words, the conductive material 907 may play a role of an electric wire between the nanowire photodetector 904 and at least one micro electrode 921.

Referring to FIG. 9k, the photoresist film 906 may be removed. As a result, the plating base 905 located below the photoresist film 906 may be partially exposed.

Referring to FIG. 9l, the exposed region of the plating base 905 may be removed. Meanwhile, the other area of the plating base 905 may not be removed since it is covered by the conductive material 907.

Referring to FIG. 9m, after the exposed region of the plating base 905 is removed, a first support layer 908 may be formed on the nanowire substrate 900 and the micro electrode substrate 920, which are bonded to each other. The first support layer 908 plays a role of a substrate supporting the nanowire photodetector 904 and the micro electrode 921 later and may be made of flexible material. In addition, the first support layer may be made of biocompatible material such as polymer or polyimide. Next, the first support layer 908 may be patterned by means of photolithography, so that a region of the nanowire photodetector 904 not covered by the conductive material 907 may be exposed.

Referring to FIG. 9n, a conductive material 909 may be formed on the exposed region of the nanowire photodetector 904. The conductive material 909 may be located at an end of the nanowire photodetector 904, which is opposite to an end where the nanowire 910 and the conductive material 907 are electrically connected, based on the location of the nanowire 901 and be electrically connected to the nanowire 901. In other words, the nanowire 901 may electrically connect the conductive materials 907, 909. The conductive material 907 and the conductive material 909 may be made of the same material or different materials. The conductive material 909 may play a role of a signal line which transmits a signal from an external device, for example a power source, to the nanowire photodetector 904.

Referring to FIG. 9o, after the conductive material 909 is completely formed, a second support layer 910 may be formed on the nanowire substrate 900 and the micro electrode substrate 920. The second support layer 910 is a component playing a role of a flexible substrate supporting the nanowire photodetector 904 and the micro electrode 921 together with the first support layer 908 described above. In addition, each of the support layers 908, 910 may play a role of protecting the conductive material 907, 909 serving as an electric wire. The second support layer 910 may be made of the same material as or a different material from the first support layer 908.

Referring to FIG. 9p, the micro electrode substrate may be removed while remaining at least one micro electrode 921. As a result, the nanowire photodetector 904 and at least one micro electrode 921 are located on the first and second support layers 908, 910 which are made of flexible material such as polymer or polyimide and play a role of a substrate. In other words, the nanowire photodetector 904 and at least one micro electrode 921 may be integrated on a flexible substrate.

A power source (not shown) separately fabricated by means of CMOS may be located on the flexible substrates 908, 910 made by integrating the nanowire photodetector 904 and at least one micro electrode 921 as described above, and a power source may be electrically connected to the nanowire photodetector 904 and the micro electrode 921 by means of wire bonding or other packaging processes. In addition, the coupled devices may be sealed by using epoxy or the like friendly to a human body.

Figure 10:
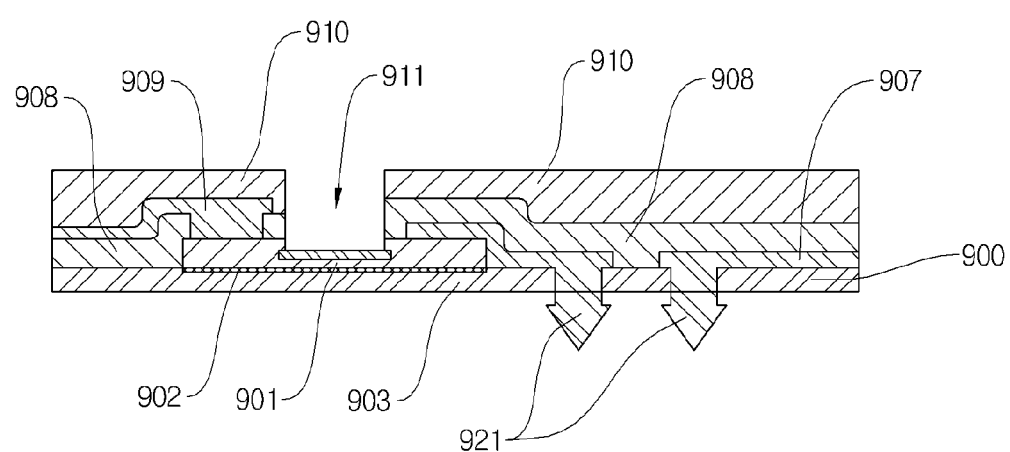
FIG. 10 is a cross-sectional view showing a retinal prosthesis system according to another embodiment.

FIG. 10 is a cross-sectional view showing a retinal prosthesis system according to another embodiment. In the description of the embodiment shown in FIG. 10, features which can be easily understood from the former embodiments by those having ordinary skill in the art will be not described, and features different from the former embodiments will be described.

Referring to FIG. 10, in the retinal prosthesis system of this embodiment, the first and second support layers 908, 910 covering the nanowire photodetector 904 and at least one micro electrode 921 have a hole 911. The hole 911 may be formed through the first and second support layers 908, 910 and be aligned with the nanowire 901 of the nanowire photodetector 904. As a result, the nanowire 901 may not be covered by the first and second support layers 908, 910 but exposed out. Therefore, the light irradiated from the outside may reach the nanowire 901 without attenuation.

Figure 11:
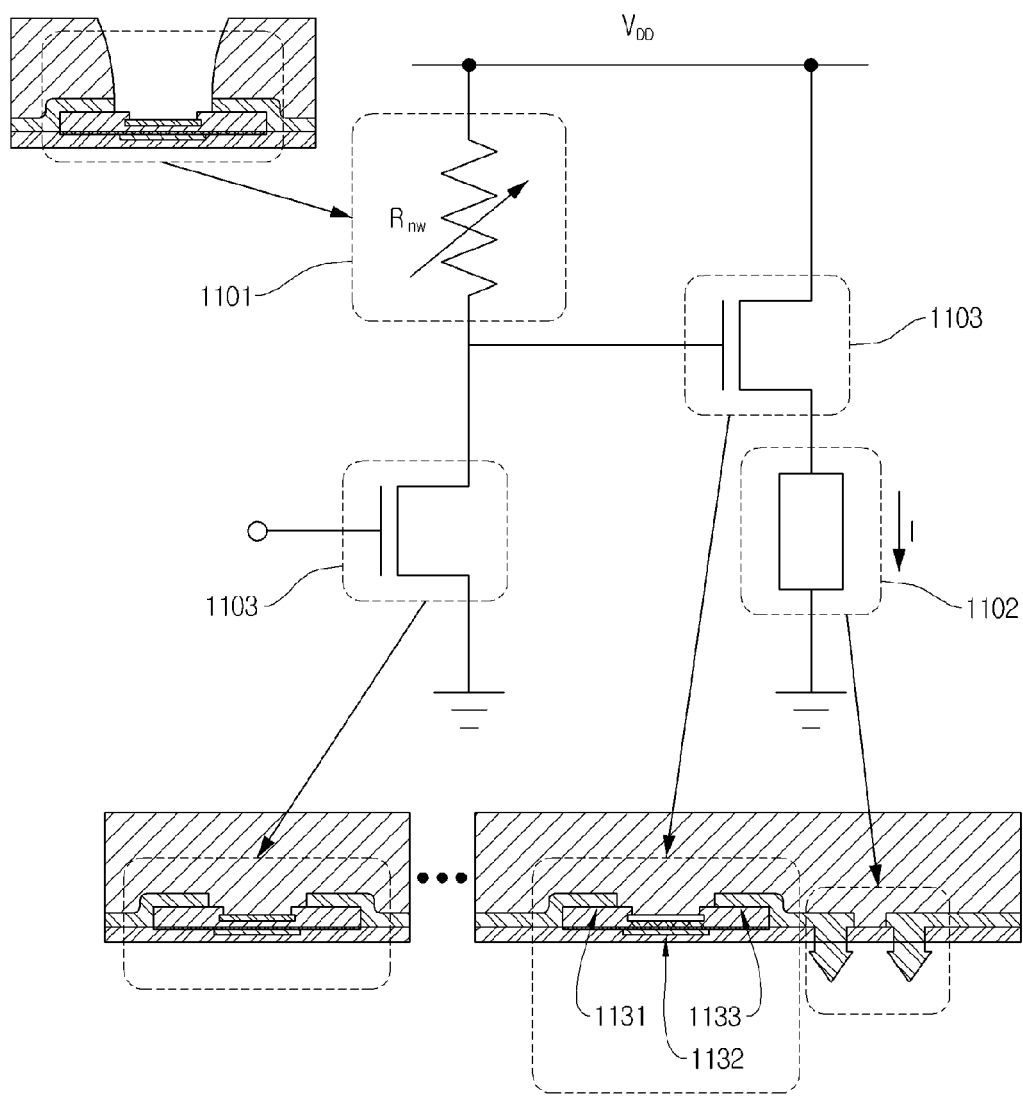
FIG. 11 is a diagram showing a retinal prosthesis system further including a nanowire field effect transistor (FET) according to another embodiment.

FIG. 11 is a diagram showing a retinal prosthesis system according to another embodiment.

Referring to FIG. 11, the retinal prosthesis system of this embodiment may further include at least one nanowire field effect transistor (FET) 1103 in addition to the nanowire photodetector 1101 and the micro electrode array 1102. Different from the nanowire photodetector 1101 which includes a pair of electrodes (for example, a source electrode and a drain electrode) respectively located at both ends of a nanowire, the nanowire FET 1103 may be configured to include a source electrode 1131, a gate electrode 1132 and a drain electrode 1133. Detailed configuration and operations of the nanowire FET 1103 may be easily understood from common FET's operations and are not described in detail here.

Each nanowire FET 1103 may be electrically connected to the nanowire photodetector 1101. For example, the nanowire FET 1103 may be electrically connected between the nanowire photodetector 1101 and the micro electrode array 1102 to amplify a signal of the nanowire photodetector 1101 and operate the micro electrode array 1102 by using the amplified signal. According to this embodiment, a circuit for signal amplification may be integrated together on a substrate where the nanowire photodetector 1101 and the micro electrode array 1102 are integrated.

While the present disclosure has been described with reference to embodiments depicted in the drawings, it is just an example and it will be understood by those skilled in the art that various changes or modifications may be made thereto. However, such modifications should be regarded as belonging to the technical scope of the present disclosure. Therefore, the true scope of the present disclosure should be decided based on the technical spirit of the appended claims.

The invention claimed is:

1. A retinal prosthesis system, comprising:
   a flexible substrate;
   a nanowire photodetector disposed on the flexible substrate and having a plurality of nanowires whose resistance varies according to an applied light;
   a plurality of micro electrodes arranged in an array pattern disposed on the flexible substrate, the micro electrode array electrically connected to the nanowire photodetector and comprising a retina-engaging portion protruding in a vertical direction from a surface of the flexible substrate for contacting a retina cell; and
   a discrete power source for providing the nanowire photodetector and the micro electrode array with a stimulation signal waveform, the power source further including a battery,
   wherein the nanowire photodetector comprises a plurality of column structures each having a nanowire, wherein each column structure includes a first portion having a first width and extending in one direction and a second portion having a second width smaller than the first width and supporting the first portion, and wherein each column structure further includes an oxide film disposed on the first portion and the second portion so that the first portion has each nanowire and the oxide film surrounds each nanowire,
   wherein the nanowire photodetector modulates a stimulation signal waveform generated by the power source according to the applied light and transmits the modulated signal to the micro electrode array, and
   wherein the micro electrode array receives the signal modulated by the nanowire photodetector and applies the modulated signal to the retina cell to stimulate the retina cell.

2. The retinal prosthesis system according to claim 1, wherein each nanowire includes silicon.

3. The retinal prosthesis system according to claim 1, wherein the substrate includes polymer or polyimide.

4. The retinal prosthesis system according to claim 1, further comprising a nanowire field effect transistor electrically connected to the nanowire photodetector to amplify a signal of the nanowire photodetector.

5. The retinal prosthesis system according to claim 1, wherein the substrate, the nanowire photodetector and the micro electrode array are configured to be transplanted in a living body.

\* \* \* \* \*